(12) United States Patent
Mendels

(10) Patent No.: US 8,034,021 B2
(45) Date of Patent: *Oct. 11, 2011

(54) MANIFOLD HUB FOR PATIENT FLUID ADMINISTRATION

(75) Inventor: Yair Mendels, Motza Elit (IL)

(73) Assignee: Biometrix Ltd., Jerusalem (IL)

(*) Notice: Subject to any disclaimer, the term of this patent is extended or adjusted under 35 U.S.C. 154(b) by 123 days.

This patent is subject to a terminal disclaimer.

(21) Appl. No.: 12/501,090

(22) Filed: Jul. 10, 2009

(65) Prior Publication Data

US 2010/0022967 A1  Jan. 28, 2010

Related U.S. Application Data

(63) Continuation of application No. 11/132,642, filed on May 19, 2005, now Pat. No. 7,563,243, which is a continuation-in-part of application No. PCT/IL03/00983, filed on Nov. 19, 2003.

(30) Foreign Application Priority Data

Nov. 19, 2002 (IL) .......................................... 152950

(51) Int. Cl.
*A61M 5/14* (2006.01)
(52) U.S. Cl. ....................................................... 604/80
(58) Field of Classification Search .................. 604/246, 604/247, 256, 533, 534, 535
See application file for complete search history.

(56) References Cited

U.S. PATENT DOCUMENTS

| | | | |
|---|---|---|---|
| 3,957,082 A | 5/1976 | Larson et al. | |
| 4,177,835 A | 12/1979 | Paley | |
| 4,257,416 A | 3/1981 | Prager | |
| 4,432,392 A | 2/1984 | Paley | |
| 4,658,834 A | 4/1987 | Blankenship et al. | |
| 5,190,525 A | 3/1993 | Oswald | |
| 5,192,269 A | 3/1993 | Poli et al. | |
| 5,217,432 A | 6/1993 | Rudzena et al. | |
| 5,250,040 A | 10/1993 | Parks et al. | |
| 5,374,248 A | 12/1994 | Lopez | |
| 5,431,185 A | 7/1995 | Shannon et al. | |

(Continued)

FOREIGN PATENT DOCUMENTS

FR  2358601  2/1978

(Continued)

OTHER PUBLICATIONS

International Search Report published Dec. 23, 2004 for PCT/IL2003/00983, filed Nov. 19, 2003.

(Continued)

*Primary Examiner* — Nicholas D Lucchesi
*Assistant Examiner* — Aarti B Berdichevsky
(74) *Attorney, Agent, or Firm* — Martin Fleit; Paul D. Bianco; Fleit Gibbons Gutman Bongini & Bianco PL

(57) ABSTRACT

The present invention concerns a housing for supporting the proximal inlet ports of at least two isolated lumens, for use in a patient fluid administration system, wherein each of the lumens further comprises a distal outlet for connecting to at least one patient fluid administration member, and wherein the housing further comprises an integral unit, wherein the unit comprises a distal frame layer, a female connector layer, for connecting to at least one of the fluid peripheral elements and at least one intermediate gasket layer for providing sealing between each of the isolated lumens.

20 Claims, 24 Drawing Sheets

U.S. PATENT DOCUMENTS

| | | |
|---|---|---|
| 5,486,159 A | 1/1996 | Mahurkar |
| 5,527,299 A | 6/1996 | Cude |
| 5,699,821 A | 12/1997 | Paradis |
| 5,738,662 A | 4/1998 | Koenig |
| 5,769,087 A | 6/1998 | Westphal et al. |
| 5,820,601 A | 10/1998 | Mayer |
| 6,036,654 A | 3/2000 | Siman et al. |
| 6,206,851 B1 | 3/2001 | Prosel |
| 6,364,861 B1 | 4/2002 | Feith et al. |
| 6,428,520 B1 | 8/2002 | Lopez et al. |
| 6,582,379 B1 | 6/2003 | Stisen |
| 6,592,544 B1 | 7/2003 | Currier et al. |
| 7,396,348 B2 | 7/2008 | Newton et al. |
| 7,563,243 B2 * | 7/2009 | Mendels ............ 604/80 |
| 2002/0161314 A1 | 10/2002 | Sarajarvi |
| 2003/0135165 A1 | 7/2003 | Chernack |
| 2005/0096627 A1 | 5/2005 | Howard |
| 2005/0121103 A1 | 6/2005 | Steigerwalt et al. |
| 2007/0255167 A1 | 11/2007 | Christensen et al. |

FOREIGN PATENT DOCUMENTS

| | | |
|---|---|---|
| FR | 2513520 | 4/1983 |
| FR | 2513520 A1 | 4/1983 |
| WO | 00/27452 | 5/2000 |
| WO | 0027452 A1 | 5/2000 |
| WO | 2010141458 A2 | 12/2010 |
| WO | 2010141563 A3 | 12/2010 |

OTHER PUBLICATIONS

International Search Report published Feb. 7, 2011 for PCT/US2010/036887, filed Jun. 1, 2010.

International Search Report published Jan. 12, 2011 for PCT/US2010/037043, filed Jun. 2, 2010.

* cited by examiner

FIG.3A
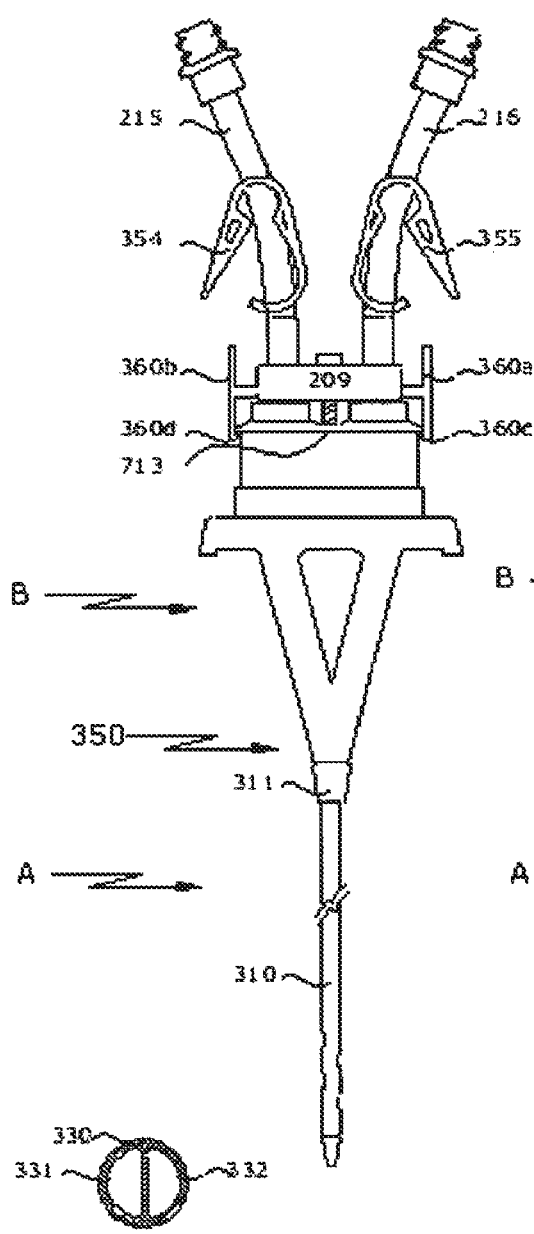
FIG.3B
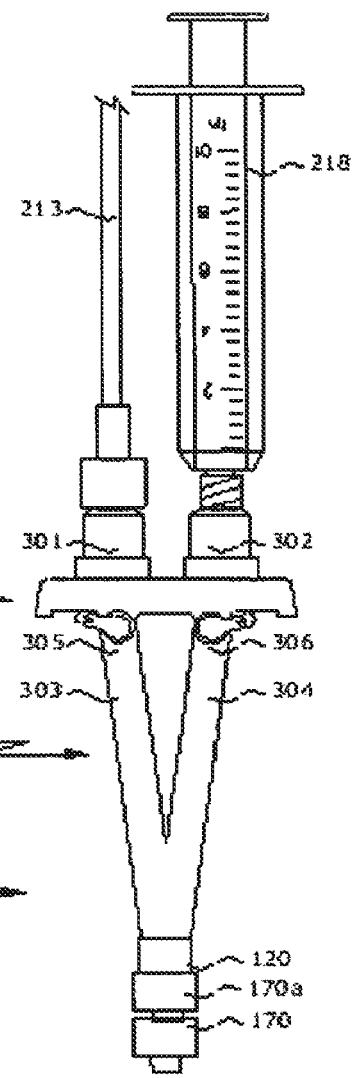
FIG.3C

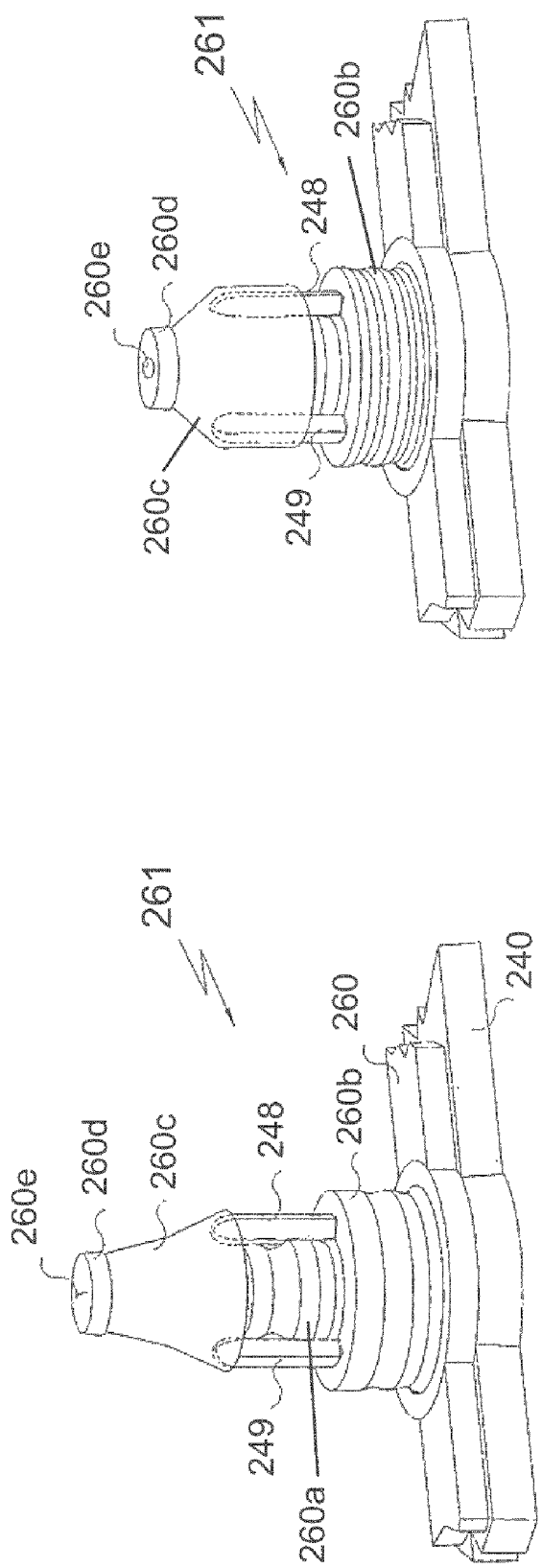

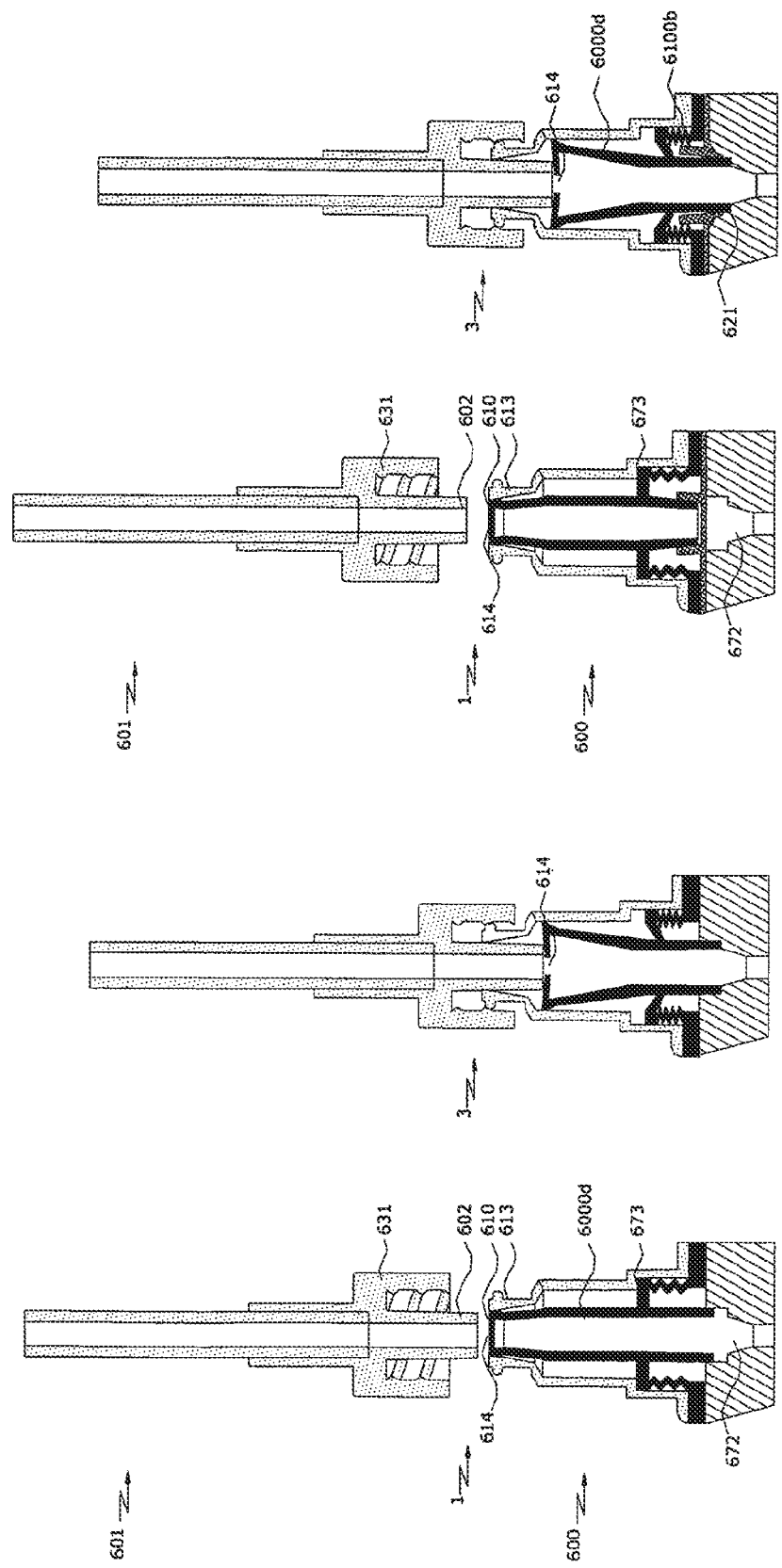

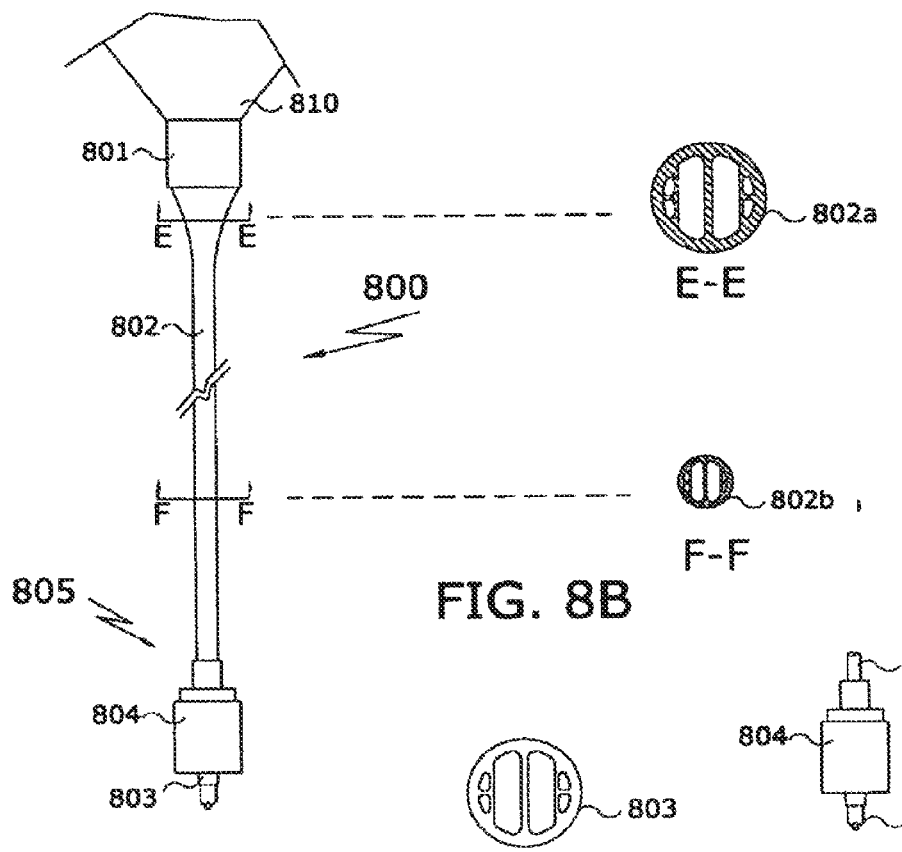
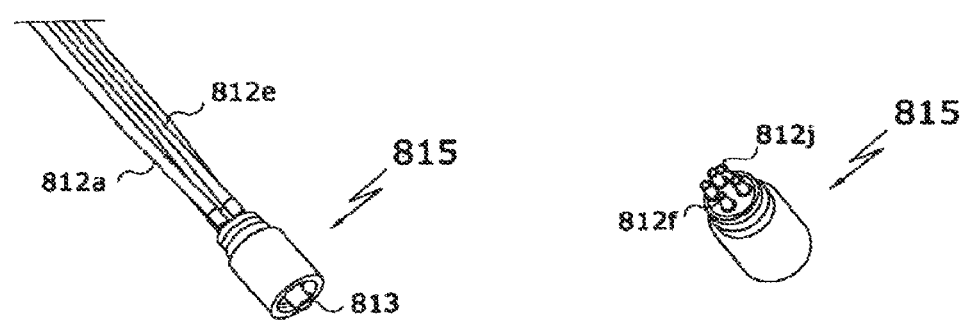
FIG. 8A  FIG. 8D  FIG. 8C
FIG. 8E  FIG. 8F

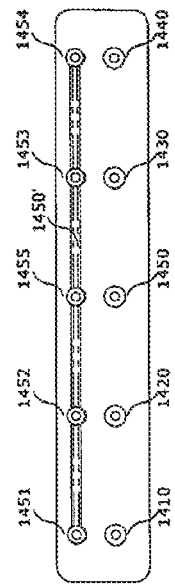
FIG.10B
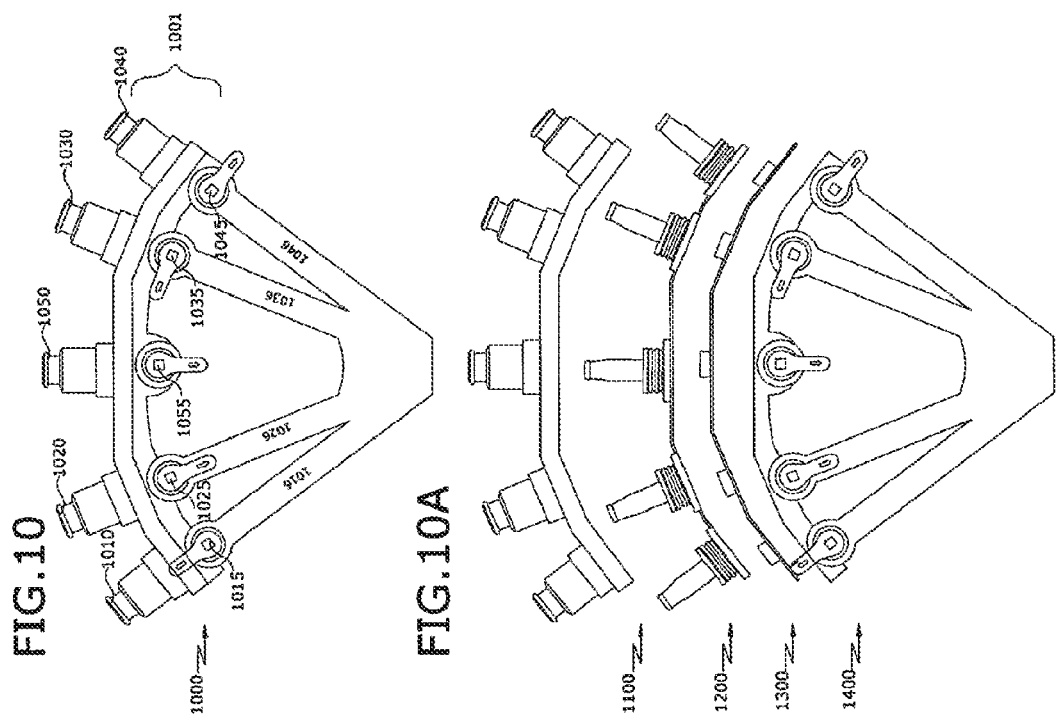
FIG.10
FIG.10A

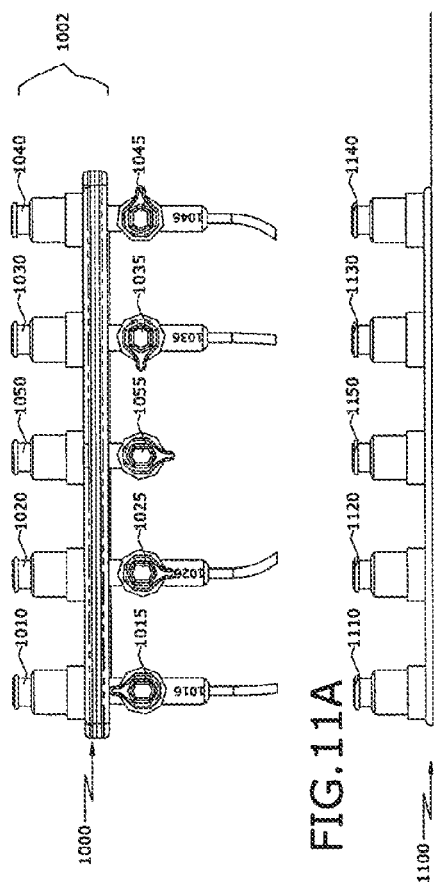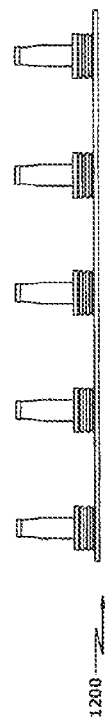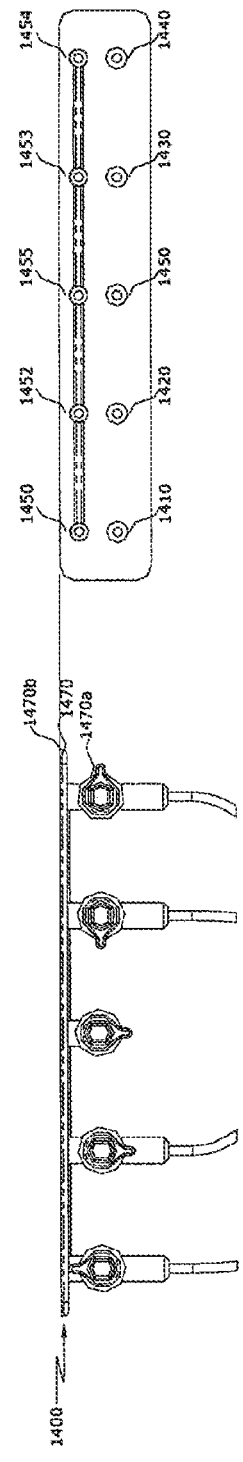

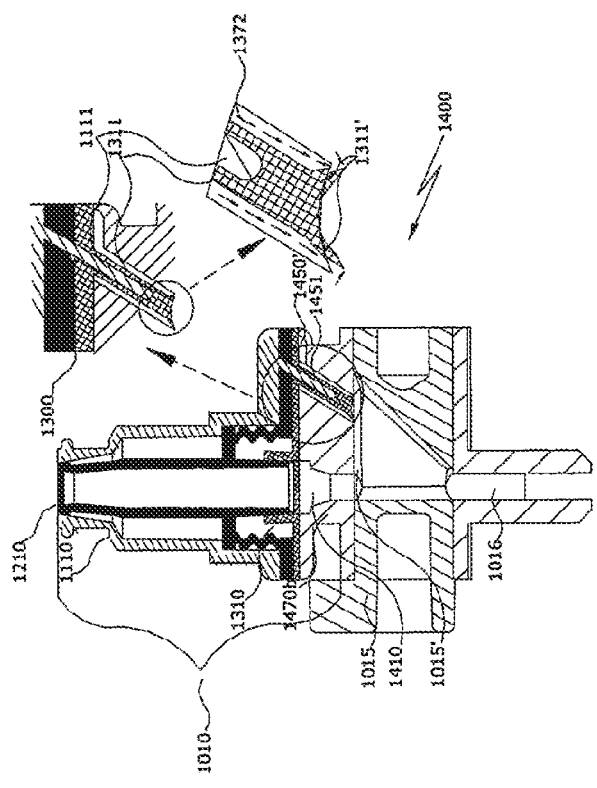
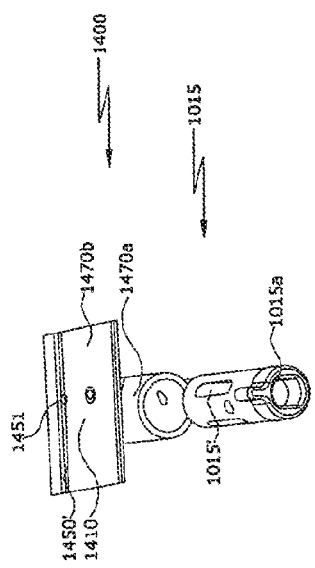
FIG. 12A
FIG. 12B

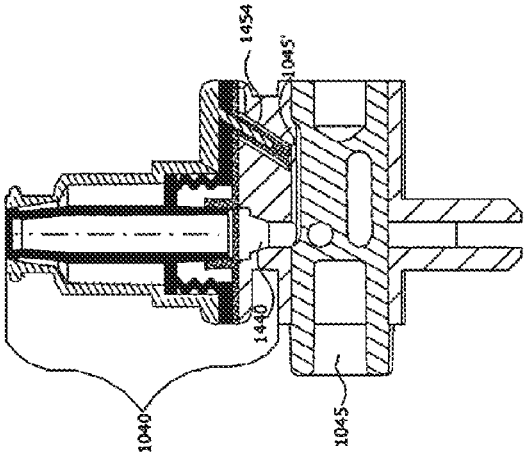
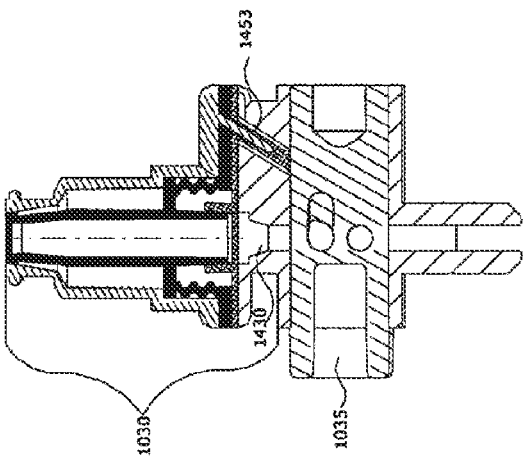
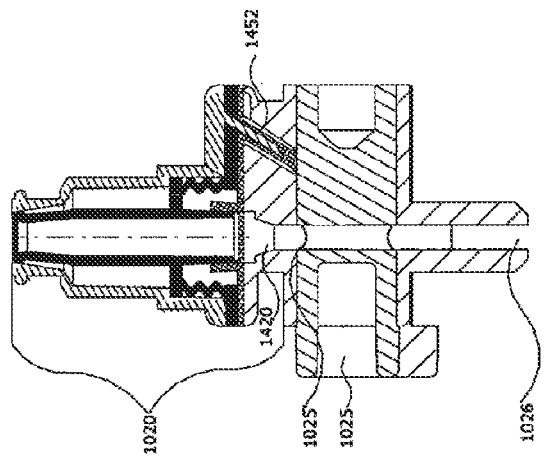
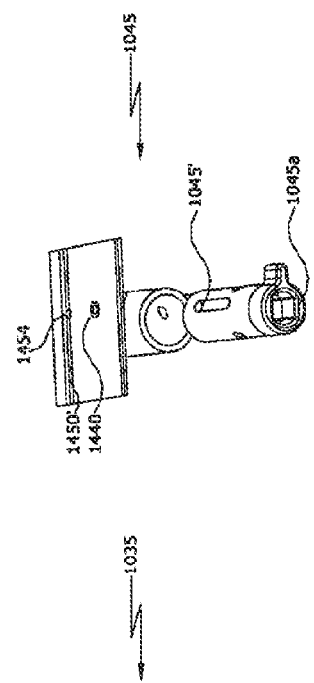
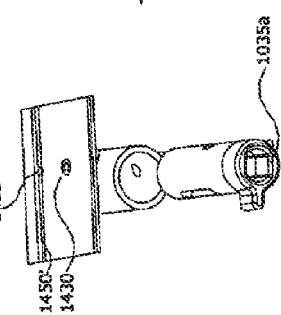
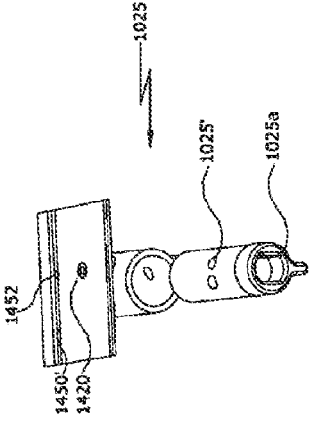

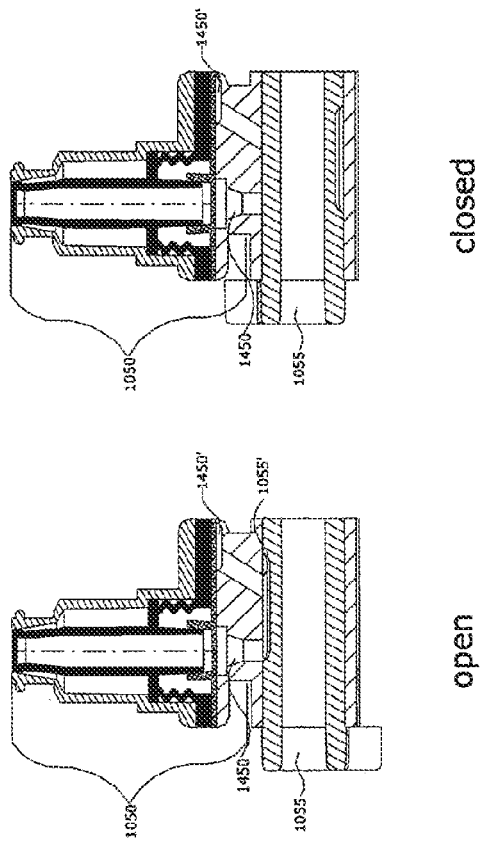
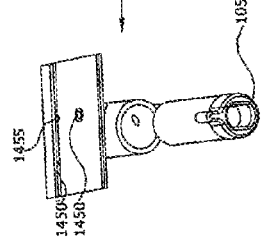
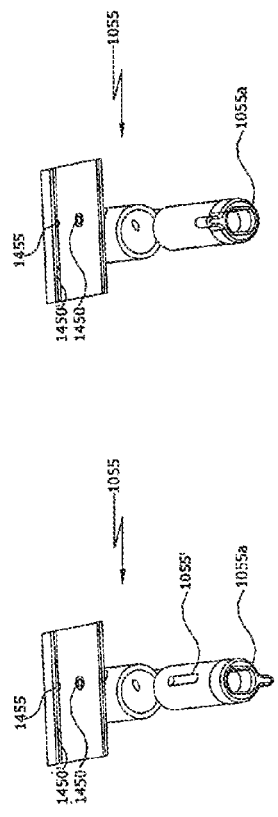
FIG.13D  FIG.13E
open    closed

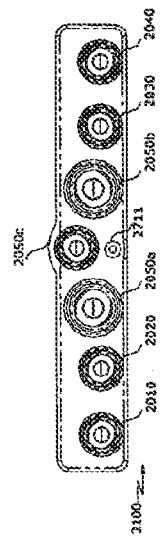
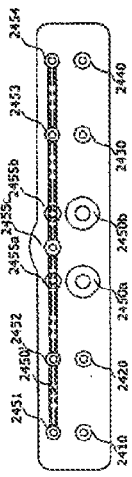
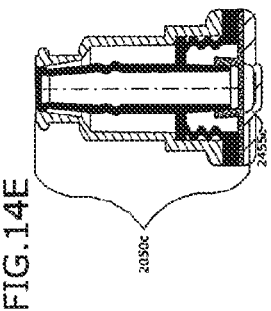
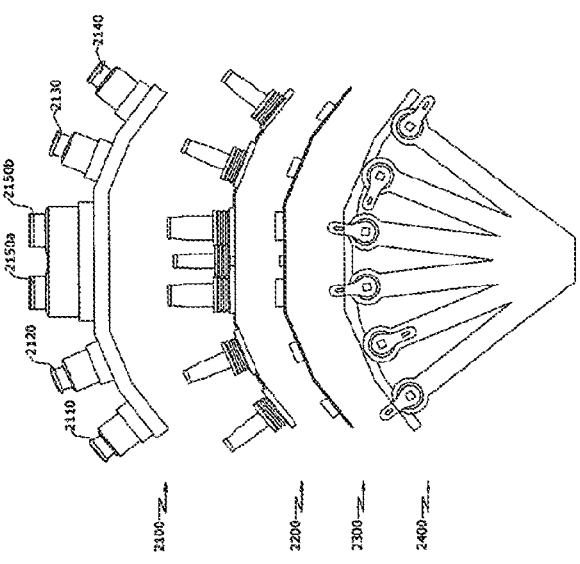
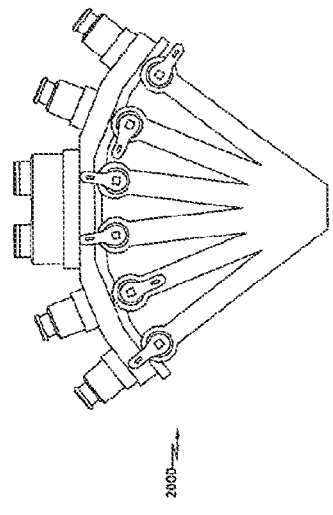
FIG.14D
FIG.14C
FIG.14E
FIG.14B
FIG.14A

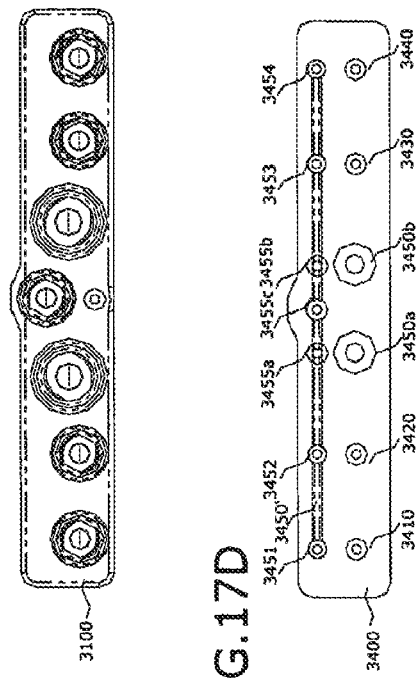
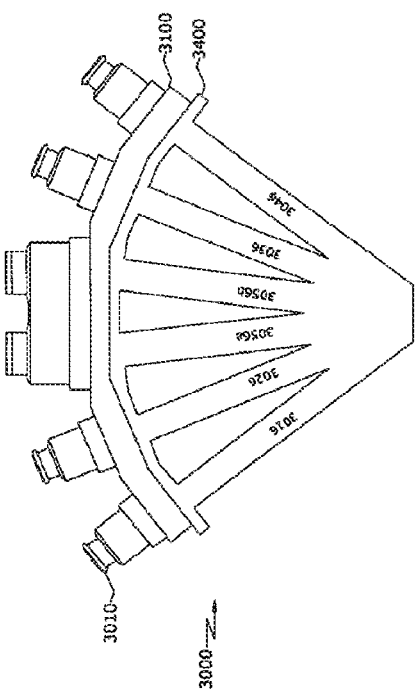
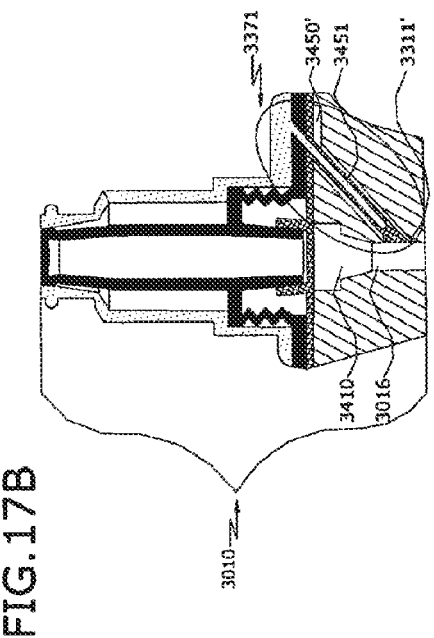

MANIFOLD HUB FOR PATIENT FLUID ADMINISTRATION

CROSS REFERENCE TO RELATED APPLICATION

This application is a continuation of U.S. patent application Ser. No. 11/132,642, filed May 19, 2005, which is a continuation-in-part of International Application No. PCT/IL2003/000983, filed Nov. 19, 2003, the content of which is expressly incorporated herein by reference thereto, which claims priority from Israeli Patent Application No. 152950 filed Nov. 19, 2002.

FIELD OF THE INVENTION

The present invention generally relates to a manifold hub for use in a fluid administration system. In particular, the present invention relates to a manifold hub which is characterized by a plurality of mutually distinct flow channels that comprise a plurality of isolated lumens. More particularly, the present invention relates to a manifold hub in the form of a housing comprising a plurality of isolated lumens.

BACKGROUND OF THE INVENTION

For the sake of clarity, the following terms, which shall be used in the present application, are to be defined as follows:

The terms "inlet" and "outlet" as used herein as referring to liquid ports, do not come to limit the use of such a port to a directional flow of the fluid, and in some cases (such as dialysis) the direction can be reversed.

The term "fluid peripheral elements", as used herein, includes any fluid reservoir that is intended to supply fluid to a patient, such as an infusion bag containing blood plasma or a therapeutic agent; various dialysis apparatus; pumps and the like. Additionally, this term may refer to any element that is intended to cause fluid to flow out from the patient such as in case of a dialysis system, that removes and reinserts blood from and into the patient respectively.

The term "patient fluid administration member" refers to any element which is connected on one side (its proximal side) to the manifold hub, and on the other side (its distal side) either directly or indirectly to an entry member, which is inserted to the patient's vascular system, or to any other orifice or vessel of the patient. Examples of "patient fluid administration members" include individual tubes, which may be single or multi lumen, or a plurality of tubes, singular or multi lumen, that may be attached to each other in a bus type configuration. These tubes, in turn, can be connected to, for example, a needle, a catheter which is fully or partially inside the patient's vascular system or other vessel, a cannula and the like. The manifold may also be connected to a multi lumen tube which is within the body of the patient, the tube forming an extension-less catheter. It should be noted that the term "patient fluid administration member" is not solely intended to denote a member capable of administering fluid into the patient but also to a member capable of removing blood from the patient to the peripheral element, for example, in dialysis.

The term "fluid administration system" as used herein, refers to a system for transferring fluid, comprising at least a manifold hub, at least one fluid peripheral element and a fluid administration member, as described below.

The term "fluid administration external infusion manifold", as used herein below, as well as a variety of particular embodiments, shall be all referred to herein in the general term "manifold" or "manifold hub". A manifold generally comprises a plurality of inlets, having a single outlet. A manifold hub, to which the present invention relates, is generally a device for connecting a plurality of inlet ports to at least one external object. In particular, the manifold hub may comprise an identical number of inlets as outlets, or, alternatively, the number of inlets may be different than that of outlets. Additionally, for simplicity's sake, although some embodiments as described herein relate to a plurality of isolated lumens joined by a single port at one end, i.e. a hub, and others, to a plurality of isolated lumens that are not joined at one end, the term "manifold hub" is used throughout.

The terms "upper" and "lower", in particular, when referring to the intermediate gasket layers of the present invention, as described herein, are meant to describe different layers of the housing of the present invention, relative to each other, and not to imply that both layers need always be present. In other words, when only the upper layer, or only the lower layer may be present, the layers are nevertheless referred to as "upper" or "lower", respectively.

The terms "sealing" and "isolated" as used herein, particularly when describing the relationship between lumens, refer to preventing at least fluid communication between lumens or flow channels.

The term "fluid", as used herein, shall refer to any liquid, solvent, diluent, saline, water, liquefied medicament as well as to any biofluid, human or other, allowed to flow out of or withdrawn from the body of a patient, including blood and blood products, plasma, nutrients and medicaments.

The term "standard" and the term "conventional" when referring to a female luer (FL) activated valve (also referred to herein as, "luer activated connector") or when referring to a male luer (ML) or Male Luerlock (MLL), generally relates to any normal, ISO, ANSI and/or universal luer activated valve type connection known in the art. High flow connectors are adapted to provide a flow of fluids in a flux higher than that allowed by the aforementioned conventional FL. A high flow connector is thus characterized by having a larger bore, and its connecting coupler is larger than a conventional luer activated connector. The term 'connector having a minimal dead space' is defined as a connector characterized by a small bore, and its connecting coupler is smaller than that of a conventional luer connector. The standard luer activated connectors as described herein preferably comprise a standard luer lock feature for the standard connector locking system and/or with any other locking feature for the high and low connector locking system.

Fluid administration external infusion manifolds are widely used for administering therapeutic fluids, into the body of a patient, from a plurality of fluid reservoirs. Currently available manifolds do not provide simultaneous infusion of a plurality of fluids in a manner such that fluids do not mix as they pass through the manifold.

Typically, a manifold, in particular, a manifold connected to a catheter device, comprises a single lumen having an outlet port, through which a fluid is transferred, to a patient. The single lumen has multiple inlet ports, each of which can be connected to a separate fluid reservoir, and valves, such as stopcock valves, for closing and opening the entry of fluid to the lumen. However, since all fluids flow through the single, common lumen, and out the same outlet port, when using the manifold, the working fluid mixes with fluid residue contained within the lumen from a previous use, which can result in undesirable interaction between the fluids.

This problem is overcome by flushing the lumen with a neutral fluid, such as saline, before administering a second fluid, in order to replace the dead space to the manifold.

It is evident that this method of cleaning the manifold from excess fluid is undesirable, as unnecessary administration of a "neutral" fluid is required.

Furthermore, prior art administration systems require much handling by the medical personnel (e.g. nurses), including rinsing, flushing and opening and closing of valves and/or stopcocks in order to remove the residue fluid. This further increases the risk of undesirable therapeutic fluid mixing.

Additional requirements of fluid administration systems include priming the manifold prior to use, wherein the entire manifold housing is primed with a predetermined solution in order to prepare the manifold for use by ensuring the lumen is free from air bubbles.

In prior art manifolds, individual connectors, such as luer activated connectors, are individually situated at each manifold inlet port for securing each of the plurality of fluid reservoirs to the ports.

A device for simultaneously administering two or more fluids to a patient, without allowing the fluids to mix, is well known, for use with catheters. The hub of a multi lumen catheter is connected in its proximal end to isolated lumen extensions that are connected to fluid reservoirs when fluid is required to be administered to the patient, and may be disconnected therefrom when not requiring fluid administration. For prior art catheters, the patient must cope with the awkwardness associated with tubes exiting the body. For instance, multi lumen catheter hub designs cause irritation when mounting in place and cause the patient discomfort when dressing and undressing. These drawbacks are particularly undesirable during long term treatments. It would therefore be beneficial to have a catheter that does not require tubes to exit the patient's body when not in use.

SUMMARY OF THE INVENTION

The present invention relates to a housing for supporting the proximal inlet ports of at least two isolated lumens, for use in a patient fluid administration system, wherein each of said lumens further comprises a distal outlet for connecting to at least one patient fluid administration member, and wherein said housing further comprises an integral unit, said unit comprising a distal frame layer, a female connector layer, for connecting to at least one of said fluid peripheral elements and at least one intermediate gasket layer for providing sealing between each of said isolated lumens.

More particularly, the present invention provides a specific embodiment of a manifold hub for use in a fluid administration system comprising an integrated housing providing a plurality of mutually distinct flow channels through the housing and being composed of at least three components. A first component serving as a connector layer comprises an elongated first member having a plurality of longitudinally spaced first openings each associated with a distinct flow channel and a plurality of longitudinally spaced upward, tubular first projections surrounding and aligned with said first openings and open at their upper and lower extremities each associated with a distinct flow channel, The first projections are formed as one part of a two-part connector. A second component serving as a distal frame layer comprises an elongated second member having a plurality of longitudinally spaced second openings each associated with a distinct flow channel and defining a plurality of longitudinally spaced separate outlets each associated with a distinct flow channel. An intermediate component serving as a gasket layer comprises an elongated third member that is resilient and has a plurality of longitudinally spaced third openings each associated with a distinct flow channel and a plurality of longitudinally spaced upward annular second projections each associated with a distinct flow channel. Each second projection surrounds a respective third opening. The second projections have closures at their upper extremities with normally closed slits defined in said closures and are open at their lower extremities. The first, second and third components are stacked together with the intermediate component between the first and second components and integrated together to form the housing with said second projections received in the first projections with the closures at the upper extremities of the second projections exposed at the upper extremities of the first projections, the second openings and the third openings being in fluid communication, the integrated components establishing the plurality of mutually distinct flow channels through the housing, and the intermediate component serving to seal the mutually distinct flow channels one from the other. A plurality of valves are mounted in the housing upstream of the plurality of longitudinally spaced separate outlets for controlling fluid flow through the plurality of mutually distinct flow channels, with each said valve associated with a distinct flow channel. Each said first projection can be connected to a fluid administration set via a terminal complementary part to said one part of the two-part connector such that when the connector is complete, the resilient second projection received in said first projection is depressed downwardly forcing the normally closed slit defined in the closure at the upper extremity thereof to open. The separate outlets of the second component can be connected to separate lumens each terminated with its own element for infusing fluid into a patient.

In another embodiment, the present invention provides a manifold hub for use in a fluid administration system comprising an integrated rigid housing providing a plurality of mutually distinct flow channels through the housing and being composed of four components. A first component comprises a rigid elongated first member having a plurality of longitudinally spaced first openings each associated with a flow channel and a plurality of longitudinally spaced, upward, tubular first projections open at their upper and lower extremities surrounding and aligned with said first openings each said first projection formed as one part of a two-part connector, and each associated with a flow channel. A second component comprises a rigid elongated second member having a plurality of longitudinally spaced second openings each associated with a flow channel, and defining a plurality of longitudinally spaced separate outlets each associated with a flow channel, said second component further defining a longitudinally extending groove laterally offset from the plurality of longitudinally spaced second openings. A first resilient intermediate component comprises an elongated third member having a plurality of longitudinally spaced third openings each associated with a flow channel and a plurality of longitudinally spaced upward annular second projections each associated with a flow channel. Each second projection surrounds a respective third opening, and has a closure at its upper extremity with a normally closed slit defined in said closure and is open at its lower extremity. A second resilient intermediate component comprises an elongated member having a plurality of longitudinally spaced fourth openings in the form of normally closed slits, each associated with a flow channel, the fourth openings surrounded by open upstanding tubular third projections. A plurality of valves are mounted in said housing downstream of said groove, each associated with a flow channel. The second component defines passageways extending from said groove to said valves. The first, second, third and fourth components are stacked together in the order of first component, first intermediate component, second intermediate component and second component and integrated together to form the rigid housing with said second projections received in the first projections with the closures at the upper extremities of the second projections exposed at the upper extremities of the first projections. The lower open extremities of said annular second projections are received in said third projections. The fourth openings are aligned with the second openings of the second component. The integrated components establish the plurality of mutually distinct flow channels through the housing. The resilient intermediate components serve to seal the groove and the mutually distinct flow channels one from the other. A plurality of valves are mounted in the housing upstream of the plurality of longitudinally spaced separate outlets for controlling fluid flow through the plurality of mutually distinct flow channels, with each said valve associated with a different distinct flow channel. Each said first projection can be connected to a fluid administration set via a terminal complementary part to said one part of the two-part connector such that when the connector is complete, the resilient second projection received in said first projection is depressed downwardly forcing the normally closed slit defined in the closure at the upper extremity thereof to open. Further, when an annular second projection is depressed upon connection of the connector in its flow channel, the lower extremity of the depressed second projection moves downwardly opening the normally closed slit of the fourth opening in said flow channel. Also, the separate outlets of the second component can be connected to separate lumens each terminated with its own element for infusing fluid into a patient. Alternatively, the separate openings can be connected to rigid lumens or tubes which terminate at a fitting that maintains the plurality of distinct flow channels and enables attachment of the plurality of distinct flow channels to the proximal input ends of a plurality of lumens terminated at their distal ends with their own elements for infusing fluid into a patient.

Preferably, the distal frame layer comprises at least two distal frame ports, and wherein said distal frame layer is situated above the proximal inlet ports of the isolated lumens, wherein at least one of the distal frame ports is aligned with a corresponding proximal inlet port of the isolated lumens.

Preferably, the distal frame layer may further comprise at least one valve for controlling fluid entry to at least one isolated lumen, wherein said valve may be positioned in at least any one of the following positions:
 a. open position, for allowing fluid to enter said lumen;
 b. closed position, for preventing fluid from entering said lumen.

According to a first embodiment, the distal frame layer further comprises at least one priming port for inserting a priming fluid thereto and a priming groove for carrying said priming fluid to at least one distal frame port, and further comprise at least one valve, wherein said valve may be positioned in at least any one of the following positions:
 a. priming position, for allowing fluid communication between the priming port and a corresponding lumen;
 b. fluid flow position, for allowing fluid communication between the distal frame port and a corresponding lumen;
 c. flushing position, for allowing fluid communication between the priming port and the distal frame port;
 d. closed position, for preventing fluid communication from taking place within said distal frame layer.

According to the first embodiment, the distal frame layer further comprises at least one valve, wherein said valve may be positioned in at least any one of the following positions:
 c. open position, for allowing fluid communication between an distal frame port and a corresponding priming groove;
 d. closed position, for preventing fluid communication between an distal frame port and a corresponding priming groove.

The female connector layer, according to the first embodiment, preferably comprises at least one priming connector selected from any one of the group comprising:
 a. standard female connector;
 b. large bore connector;
 c. small bore connector.

The priming connector is optionally a luer activated type connector.

Preferably, the priming connector is situated above the priming port.

According to all embodiments, the female connector layer preferably comprises at least two female connectors, wherein each connector may be selected from any one of the group comprising:
 a. standard female connector;
 b. large bore connector;
 c. small bore connector.

According to all embodiments, the connector may be a luer activated type connector.

According to all embodiments, any one of a large bore and small bore male connector may mate with its corresponding female connector. Additionally, any one of a large bore and small bore cover is adapted to cover its corresponding female connector. In these cases, any one of the large and small bore cover and large and small bore male connector is secured to its corresponding by any mechanical means such as a screw.

According to all embodiments, the at least one intermediate gasket layer comprises any one of the group consisting of:
 a. lower gasket layer;
 b. upper gasket layer;
 c. lower and upper gasket layers.

According to a first aspect, the lower gasket layer comprises an elongated flat portion having at least two slots, wherein said slots are open when in use, for fluid to flow therethrough, and sealed when not in use, thereby preventing fluid from flowing therethrough.

According to a second aspect, the lower gasket layer further comprises at least two lower gasket members spaced along the elongated flat portion and protruding upwards therefrom, wherein said lower gasket members comprise an O-ring configuration, wherein at least one slot is situated beneath a corresponding lower gasket member, and wherein said lower gasket member is aligned above the proximal inlet port of a corresponding lumen. The lower gasket layer may further comprise a gasket extension depending therefrom, for lodging within the priming port.

According to the second aspect, an outwardly extending flange may be situated at the lower end of the gasket extension, wherein in a forward fluid flow position, said flange bends in the direction of said fluid flow, for allowing fluid to flow out of the priming port, and wherein in a retrograde fluid flow position, said flange is in contact with the inner wall of said priming port, thereby preventing fluid flow into said priming port.

Preferably, according to the second aspect, a rigid stem depends from the female connector, and wherein said stem is lodged in the gasket extension for providing rigid support thereto.

According to a third aspect the lower gasket layer comprises a gasket extension depending therefrom, for lodging within the priming port.

According to the third aspect, an outwardly extending flange may be situated at the lower end of the gasket extension, wherein in a forward fluid flow position, said flange bends in the direction of said fluid flow, for allowing fluid to flow out of the priming port, and wherein in a retrograde fluid flow position, said flange is in contact with the inner wall of said priming port, for preventing fluid flow into said priming port.

Preferably, according to the third aspect, a rigid stem depends from the female connector, and wherein said stem is lodged in the gasket extension for providing rigid support thereto.

According to a fourth embodiment, the upper gasket layer comprises an elongated flat portion and at least two upper gasket members spaced along said elongated flat portion and protruding upward therefrom, wherein at least one of the upper gasket members is aligned above a proximal inlet port of a corresponding lumen.

According to the fourth aspect, the upper gasket member further comprises a hollow channel portion, having at its upper end, a truncated conical portion, wherein said upper end further comprises a flat top portion and a slot at said flat top portion for allowing fluid to pass through when in use, and for preventing fluid from passing through when not in use.

Preferably, according to the fourth aspect, the upper gasket member further comprises an outer sleeve portion at its lower end, for providing support to the hollow channel portion.

Preferably, according to the fourth aspect, upon longitudinally compressing the upper gasket member, the slot opens for fluid to pass therethrough.

According to a fifth aspect, the upper gasket layer further comprises a gasket extension depending therefrom for lodging within the priming port.

According to the fifth aspect, an outwardly extending flange may be situated at the lower end of the gasket extension, wherein in a forward fluid flow position said flange bends in the direction of said fluid flow, for allowing fluid to flow out of the priming port, and wherein in a retrograde fluid flow position, said flange is in contact with the inner wall of said priming port, for preventing fluid from flowing within said priming port.

Preferably, according to the fifth aspect, a rigid stem depends from the female connector, wherein said stem is lodged in the gasket extension for providing rigid support thereto.

According to a sixth aspect, the at least one intermediate gasket layer comprises a lower layer according to any one of the aspects as described above, and an upper gasket layer comprising an elongated flat portion and at least two upper gasket members spaced along said elongated flat portion and protruding upward therefrom, wherein at least one of the upper gasket members is positioned above a proximal inlet port of a corresponding lumen.

According to the sixth aspect, the upper gasket member comprises a hollow channel portion, having at its upper end, a truncated conical portion, wherein said upper end further comprises a flat top portion and a slot at said flat top portion for allowing fluid to pass through.

Preferably, according to the sixth aspect, the upper gasket member further comprises an outer sleeve portion at its lower end, for providing support to the hollow channel portion.

Preferably, according to the sixth aspect, upon longitudinally compressing the upper gasket member, the slot opens for fluid to pass therethrough.

According to a seventh aspect, the at least one intermediate gasket layer comprises a lower layer according to any one of the aspects as described above, and an upper gasket layer comprising an elongated flat portion and at least two upper gasket members spaced along said elongated flat portion and protruding upward therefrom, wherein at least one of the upper gasket members is aligned above a proximal inlet port of a corresponding lumen.

According to the seventh aspect, the upper gasket member further comprises a hollow channel portion, having at its upper end, a truncated conical portion, wherein said upper end further comprises a flat top portion and a slot at said flat top portion for allowing fluid to pass through when in use, and for preventing fluid from passing through when not in use.

Preferably, according to the seventh aspect, the upper gasket member further comprises an outer sleeve portion at its lower end, for providing support to the hollow channel portion.

Preferably, according to the seventh aspect, upon longitudinally compressing the upper gasket member, the slot opens thereby allowing fluid to pass therethrough.

According to all aspects, the distal frame layer may further comprise at least one integral outlet port with permanently connected lumens.

Preferably, each of the permanently connected lumens comprises an outlet port selected from any one of the group comprising:
   a. female luer connectors;
   b. male luer connectors.

According to all embodiments, the distal outlets may be joined by at least one single multi lumen port located at the distal outlet of each isolated lumen.

Preferably, the multi lumen port may be selected from any one of the group comprising:
   a. a male connector;
   b. a female connector.

Optionally, the multi lumen port mates with a corresponding connector by any one of the following:
   a. threaded connection;
   b. snap connection.
   c. snug fit connection The present invention further relates to a method for manufacturing a housing for supporting the proximal inlet ports of at least two isolated lumens, for use in a patient fluid administration system, wherein each of said lumens further comprises a distal outlet for connecting to at least one patient fluid administration member, and wherein said housing further comprises an integral unit, said method comprising:
   a. providing a distal frame layer;
   b. providing a female connector layer, for connecting to at least one of said fluid peripheral elements;
   c. providing at least one intermediate gasket layer for providing sealing between each of said isolated lumens;
   d. sealingly joining said distal frame layer with said female connector layer, wherein said at least one intermediate gasket layer is situated in between said distal frame layer and said female connector layer.

Preferably, the method further relates to providing an at least one intermediate gasket layer may comprise any one of the group comprising:
   a. upper gasket layer;
   b. lower gasket layer;
   c. lower and upper gasket layer.

BRIEF DESCRIPTION OF THE FIGURES

The present invention will be further explained in detail by the Figures. These figures are solely intend to illustrate several preferred embodiments of the present invention, and in no manner intend to limit the scope of this invention to the illustrated figures. It should be appreciated that a large variety of changes could be performed to the illustrated embodiments by those who skill in the art without departing from the scope of this invention.

FIG. 3A illustrates an embodiment of a manifold having two isolated lumens, as being accessed by peripheral elements, and having a converging adapter connected to its multi lumen port.

FIG. 3B illustrates another embodiment of manifold having two isolated lumens, used with a catheter.

FIG. 3C illustrates a lateral cross sectional view of the catheter of FIG. 3B.

FIG. 5 illustrates the inner construction and shape of one embodiment of a female port of the manifold, as it is seen in an initial position (i.e. before being accessed by a matching male connector).

FIG. 5A illustrates the inner construction and shape of the embodiment of FIG. 5, after being accessed by a matching male connector.

FIGS. 6A, 6B, 6C, 6D, 6E and 6F illustrate six different embodiments of multi layer construction of female ports of the manifold, wherein FIGS. 6A-6D show three different operational states and FIGS. 6E and 6F show two operating states.

FIGS. 8A to 8F illustrate different embodiments and views of extension members according to the present invention.

FIGS. 10, 10A and 10B illustrate an alternative embodiment of the assembled (FIG. 10) and exploded (FIG. 10A) views of the manifold hub of the present invention, showing the priming ports and groove (FIG. 10B).

FIGS. 11, 11A, 11B, 11C, 11D, and 11E illustrate other alternative embodiments comprising the priming features of the manifold hub of the present invention.

FIGS. 12A' and 12B" illustrate the view of FIGS. 12A and 12B, wherein only the upper gasket layer is present.

FIGS. 13A and 13A' illustrate the views of FIGS. 12A and 12B, with the stopcock valve for the female connector in the fluid flow position.

FIGS. 13B and 13B' illustrate the views of FIGS. 12A and 12B, with the stopcock valve for the female connector in the closed position.

FIGS. 13C and 13C' illustrate the views of FIGS. 12A and 12B, with the stopcock valve for the female connector in the flushing position.

FIGS. 13D and 13D' illustrate the views of FIGS. 12A and 12B, with the stopcock valve for the female priming connector in the open position.

FIGS. 13E and 13E' illustrate the views of FIGS. 13D and 13D', with the stopcock valve for the female priming connector in the closed position.

FIGS. 14A, 14B, 14C, 14D and 14E illustrate a further embodiment of the priming manifold of the present invention, wherein the priming connector is situated along the priming groove respectively, FIG. 14A showing an assembled side view, FIG. 14B an exploded view, 14C a top view of the distal frame layer or component showing the priming groove, 14D a top view of the connector or proximal frame layer or component showing the priming input, and 14E a vertical midsectional view showing the priming connector.

FIGS. 17A, 17B, 17C and 17D illustrate a further embodiment of the priming manifold of the present invention, similar to that of FIGS. 14A, 14B, 14C and 14D, but without valves.

DETAILED DESCRIPTION OF THE INVENTION

The present invention relates to a manifold useful for simultaneous administration of fluids via a plurality of isolated lumens or flow channels, whose distal outlets are maintained separate or joined together by a single port, wherein the proximal inlet ports are via connectors that are supported by an integral housing unit, which comprises an upper layer, a lower layer and at least one intermediate gasket layer for providing a sealing between each isolated flow channel or lumen.

Figure 1:
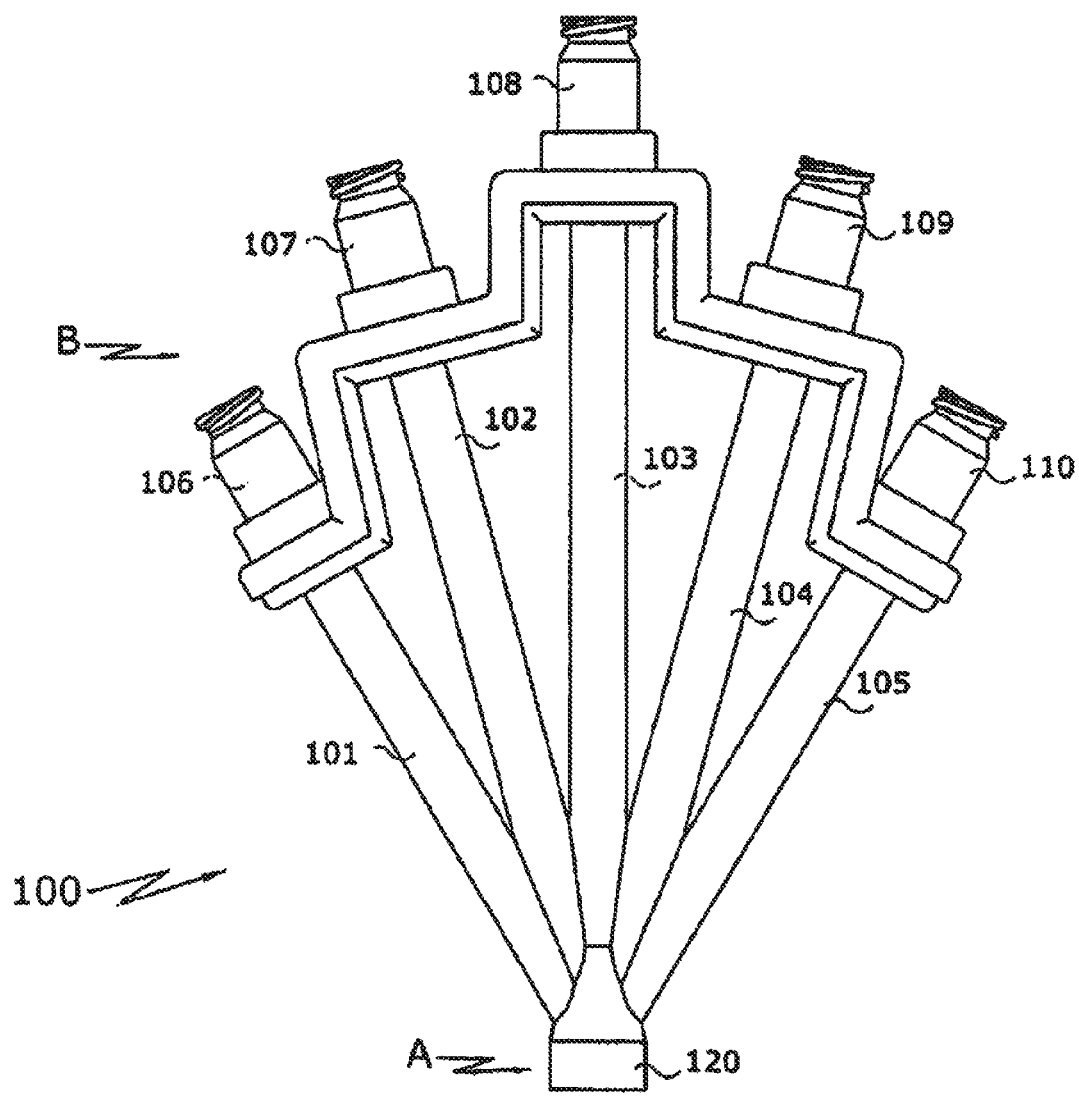
FIG. 1 illustrates a front view of one embodiment of a manifold hub according to the present invention.

FIG. 1, illustrates a front view of one embodiment of a manifold (100) according to the present invention. This manifold (100) is especially useful for simultaneous administration or draining of fluids via a plurality of isolated flow channels or lumens (101)-(105). The manifold has a distal end (A) through which the manifold is meant to communicate with a patient's body, and a proximal portion (B), through which the manifold is meant to communicate with a plurality of peripheral elements. The isolated lumens (101)-(105), are joined together by a multi lumen port (120) at the distal end (A) of the manifold, such that mixing of fluids is not possible at any portion of the manifold. Thus, fluid may be administered from a plurality of peripheral elements to a body of a patient through a multi lumen connection. This connection, through which all the lumens continue distinctly, is comprised of two multi lumen connectors, namely, the multi lumen port (120) that is an integral part of the manifold, and a multi lumen plug ((221) of FIG. 2), that is the proximal part of the interface with the patient.

The manifold is preferably comprised of a polymeric body, wherein its proximal portion (B) contains an array of female luer connectors (106)-(110), preferably assembled in a multilayer structure, as will further be detailed respective to several different embodiments illustrated herein below.

The isolated lumens may be arranged in a concentric conical configuration, or along an essentially flat plane or in any other desired configuration. The support structure may be formed as a frame or as a block, for housing the isolated lumens and establishing the mutually distinct flow channels.

Figure 1D:
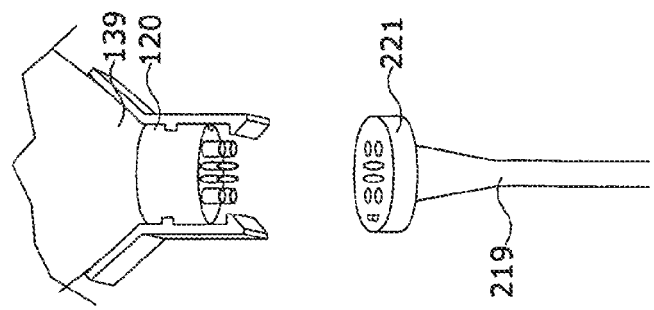
FIGS. 1A, 1B, 1C, 1D, 1E and 1F illustrate several embodiments of a multi lumen port and a matching multi lumen plug, according to the present invention.
Figure 1C:
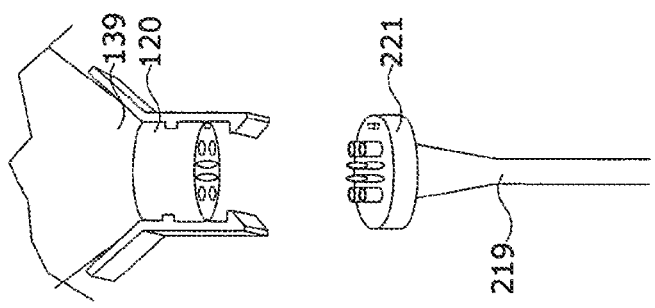
Figure 1B:
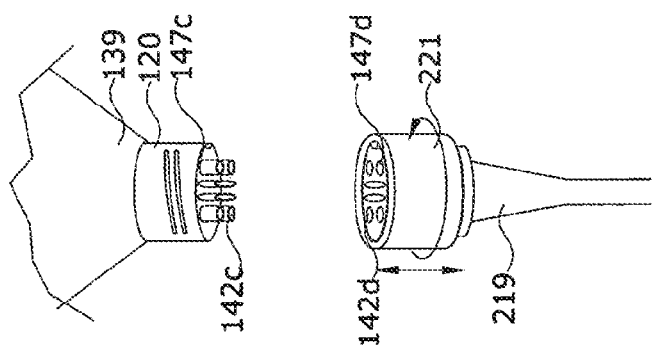
Figure 1A:
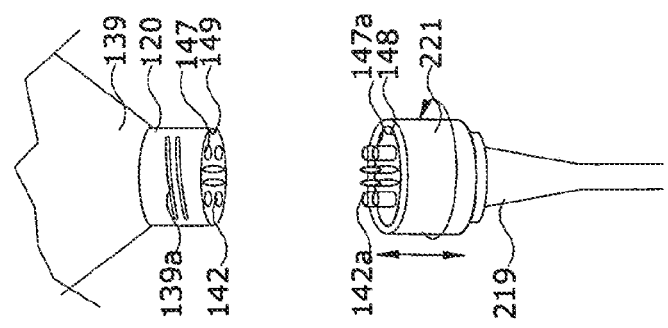

FIG. 1A illustrates one preferred embodiment of a multi-lumen connection according to the present invention. The multi-lumen connection is comprised of the multi-lumen port (120), located at the distal portion (139) of a manifold of the invention, and of the multi lumen plug (221) of an external or internal multi lumen tube (219). The multi-lumen port (120) comprises the lower ends (142)-(147) of six isolated lumens of the manifold (100), and optionally has a connective thread (139a) matching a corresponding thread existing in the multi lumen plug (221). The multi lumen plug (221) comprises the protruding upper ends (142a)-(147a) of six distinct lumens for connecting to the lower ends of isolated lumens (142)-(147). The multi lumen connection further comprises connection directive protrusion (148) and recess (149) for aiding and alignment of the connection.

The multi lumen connection enables each of the protruding lumen ends (142a)-(147a) to separately communicate with corresponding lumen ends (142)-(147). Thus, a continuity of separate fluid flow lumens is maintained, from each of the peripheral elements through the distal end of the manifold and to the patient.

FIG. 1B illustrates another embodiment of the multi lumen co connection, differing from that of FIG. 1A in that the multi lumen port (120) of the distal end (139) of the manifold of FIG. 1B comprises protruding lumen ends (142c)-(147c), while the multi lumen plug (221) has non-protruding lumens (142d)-(147d), for receiving the protruding lumen ends (142c)-(147c) of the multi lumen port (120).

FIGS. 1C and 1D illustrate further embodiments of the multi lumen connection, differing from that of FIGS. 1A and 1B, respectively, in that the connection is made by a snap-on connection, instead of by a threaded connection.

Alternatively, FIGS. 1A, 1B, 1C and 1D may be connected together by a press-fit connection (not shown in the figures.

Figure 1H:
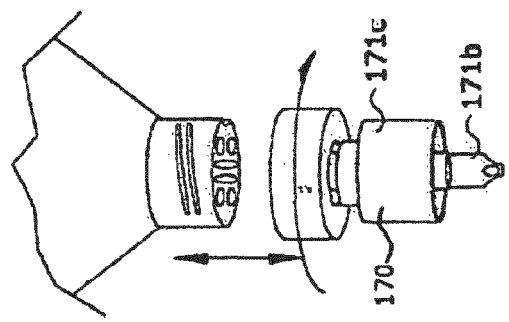
FIGS. 1G and 1H illustrate embodiments of a converging adapter according to the present invention.
Figure 1G:
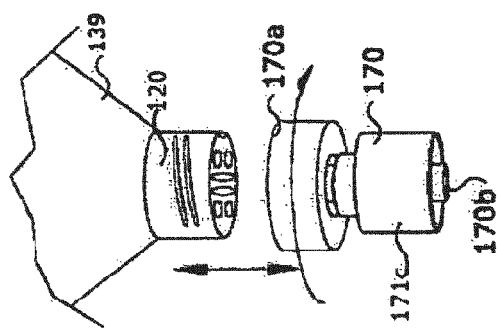
Figure 1F:
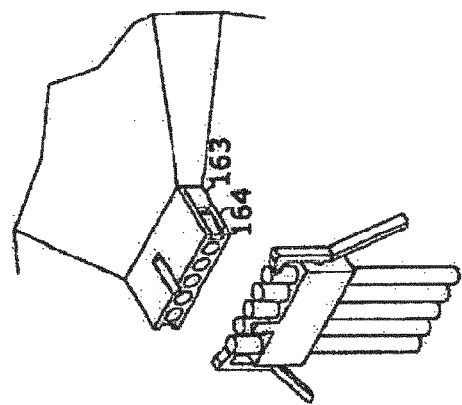
Figure 1E:
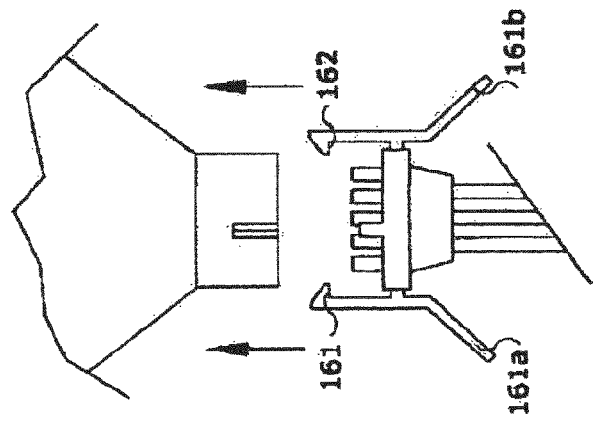

FIGS. 1E and 1F illustrate further embodiments of the multi lumen connection differing from that of FIGS. 1A and 1B, 1C and 1D, respectively, in that there are multiple tubes or lumens in FIGS. 1E and 1F, aligned in a straight array. In FIGS. 1E and 1F, the details of the snap-on connection can be more clearly observed. The connection is secured by means of two protrusions (161), (162) adapted to snap over the matching recess (163) located at the end of a guiding slope (164). Pressing the opposite ends (161a), (161b) of the protrusions (161), (162) permits easy disconnection, when required.

It should be appreciated that the number of lumens in the multi lumen connection, their sizes and respective positioning, as well as the connection methods, are not restricted to those illustrated in this detailed description, thus may be changed or varied without departing from the scope of the present invention.

FIG. 1G illustrates the multi lumen connection of FIG. 1A with its multi lumen port (120) accessed by a converging adapter (170). According to one embodiment, the converging adapter (170) has a multi lumen end (170a) and a single lumen end (170b), wherein the lumens of the multi lumen end (170a) communicate with the lumen of its single lumen end (170b). The multi lumen end (170a) connects to the multi lumen port (120) of the manifold, and the single lumen end (170b) faces the interface plug of an entry member (not illustrated). This arrangement allows for a connection between the manifold and a single lumen entry member, with the mixing of fluids taking place only in very close proximity to the entrance to the patient's vascular system.

According to another embodiment, the converging adapter (170) is single lumen on both of its ends.

According to both embodiments the flange (171c) of the converging adapter (170), together with its single lumen end (170b) could be designed either as a standard connector, e.g. luer type, or as any other type of connector. According to another embodiment, the converging adapter (170) is multi lumen on both of its ends, as illustrated in FIG. 1H by multi lumen tip (171b).

The flange (171c) of the converging adapter (170) together with its multi lumen tip (171b) (FIG. 1H), could be either a standard connector, e.g. luer type, or a different type connector. According to this embodiment the mixing of fluids can occur only outside the multi lumen tip (171b).

Figures 2, 2A:
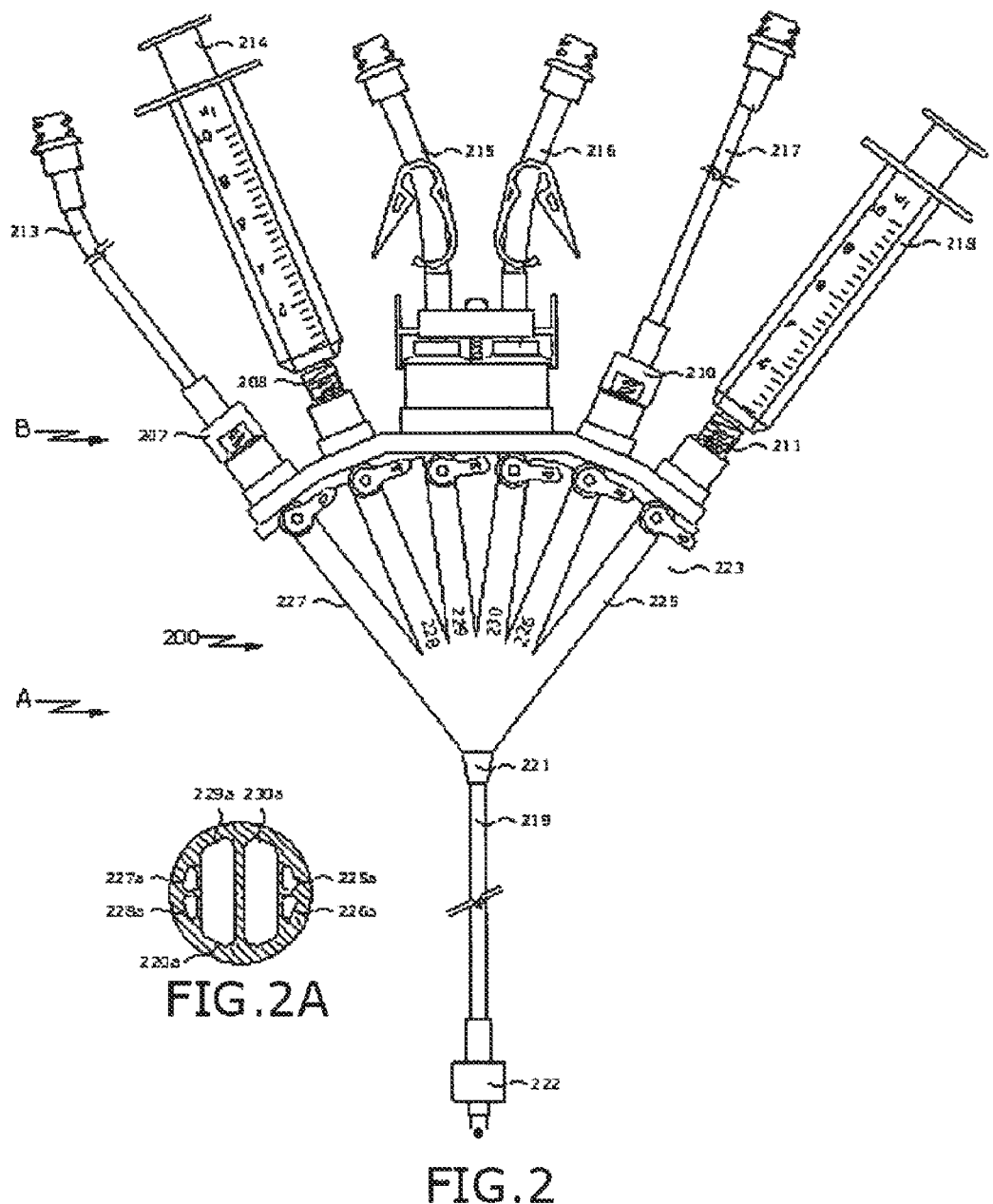
FIG. 2 illustrates an embodiment of manifold hub according to the present invention, being accessed by peripheral devices.
FIG. 2A illustrates a lateral cross sectional view of a multi lumen tube that is connected to the manifold of FIG. 2.

FIG. 2 illustrates a manifold (200), connected at its proximal portion (B) to a plurality of peripheral elements, such as a syringe (214), (218), double tubing (215), (216) of a dialysis machine, and other equipment tubing (213) (217), through an array of female connectors. Each peripheral element is connected to one of the array of female connectors by a corresponding male connectors (207)-(211).

It should be noted that the manifold, according to the present invention, is shown in this detailed description with luer type connectors only as an example. Any type of connective methods or a combination thereof, in particular, any needle-less entry connector could be used as well, without departing from the scope of this invention.

The manifold (200) communicates with a body of a patient through a multi lumen tubing (219), (i.e. the patient fluid administration member), which is connected at one end to the manifold (200) by means of the connector (221), and connected at its other end to a body invasive infusing device (not illustrated) such as a catheter or a needle, by means of a standard male or any other type connector (222), thereby allowing for coupling any desirable device having a matching (standard or other type) connector.

The manifold (200) differs from that of FIG. 1, in that the number of the lumens is six (instead of five) and in that each of the lumens (225)-(230) is provided with a valve (or, stopcock) (223), enabling a user to control the flow of the fluids through the lumens. The number of lumens and valves that are provided can be independently determined from the specific requirements and design considerations, and may vary from one embodiment to another without departing from the scope of the present invention. As an example, the number of lumens in a manifold is between 2 and 8, and could be arranged respect to one another in any convenient two or three dimensional array. For example, a manifold having six isolated lumens could be manufactured either as a two dimensional array, i.e. with the six lumens angularly spaced from one another in a single plane (as illustrated in FIG. 2), or as a three dimensional array, e.g. with the six lumens arranged in two parallel planes, each containing three angularly spaced lumens.

Furthermore, the manifold (200) differs from that of FIG. 1, in that the housing is arranged in an arc, rather than in a stepped configuration as in the embodiment of FIG. 1. This, too, is a matter of design considerations, and merely serves as illustrative examples of two different embodiments.

FIG. 2A illustrates a lateral cross section of the multi lumen tubing (219). Six cross sectional areas (225a)-(230a) could be observed, each of which corresponds to a separate lumen of the manifold (200) of FIG. 2. The different cross sectional areas (225a)-(230a) illustrate the way multi lumen tubing can be designed to conform to system requirements, wherein for the high flow connector (209), which connects the double tubing (215), (216) of the dialysis machine, larger areas (229a), (230a) are provided within the multi lumen tubing (219).

FIG. 3A illustrates a double lumen manifold (300), having two female luer connectors (301), (302) at its proximal end (B). One connector (302) is connected to a syringe (218) and the other connector (301) is connected to another peripheral element (not shown) through the tubing (213). The connectors (301), (302) individually communicate with a converging adapter (170) (according to any of its embodiments referred by the text of FIGS. 1G and 1H) that is connected to the double lumen port (120) by means of the multi lumen end plug (170a) located at the distal end (A) of the manifold (300). Two valves (305) and (306) control the fluid flow through the lumens (303) and (304), respectively.

FIG. 3B illustrates another embodiment of a double lumen manifold (350). This embodiment differs from that of FIG. 3A in that the lumens do not contain valves for controlling the flow of the fluids through its lumen, and in that it has a double port at its proximal end (B), adapted to receive a double tubing connector (209) which is the interface of a dialysis machine (not shown). The double tubing connector (209) is secured to the manifold double port by means of a clamp (360a), (360b) and protrusion (360c), (360d) connection, and further (or optionally) by means of a screw (713). Each of the tubes (215) and (216) that is connected by the double tubing connector (209) is equipped with a clamp ((354) and (355) respectively), which allows the fluid to flow through the tubing. Although the clamps are illustrated in a top view, in their actual position, with respect to the tubes, they are rotated in a 90 degree angle respective to the illustration plane. Each tubing (215) and (216) separately communicates with a double lumen catheter (310) that is connected by means of a double lumen connector (311) located at the distal end (A) of the manifold (350). It should be appreciated that without departing from the scope of the present invention one may construct the double lumen catheter (310) as an integral extension of the double lumen manifold (350), i.e. without a double lumen connector (311), but with an integral non detachable connection between the catheter (310) and the manifold (350).

FIG. 3C illustrates a lateral cross section (330) of the catheter multi lumen tube (310) of FIG. 3B. Two cross sectional areas (331) and (332) can be observed, each of which corresponds to one lumen of the manifold (350) of FIG. 3B.

Figure 4:
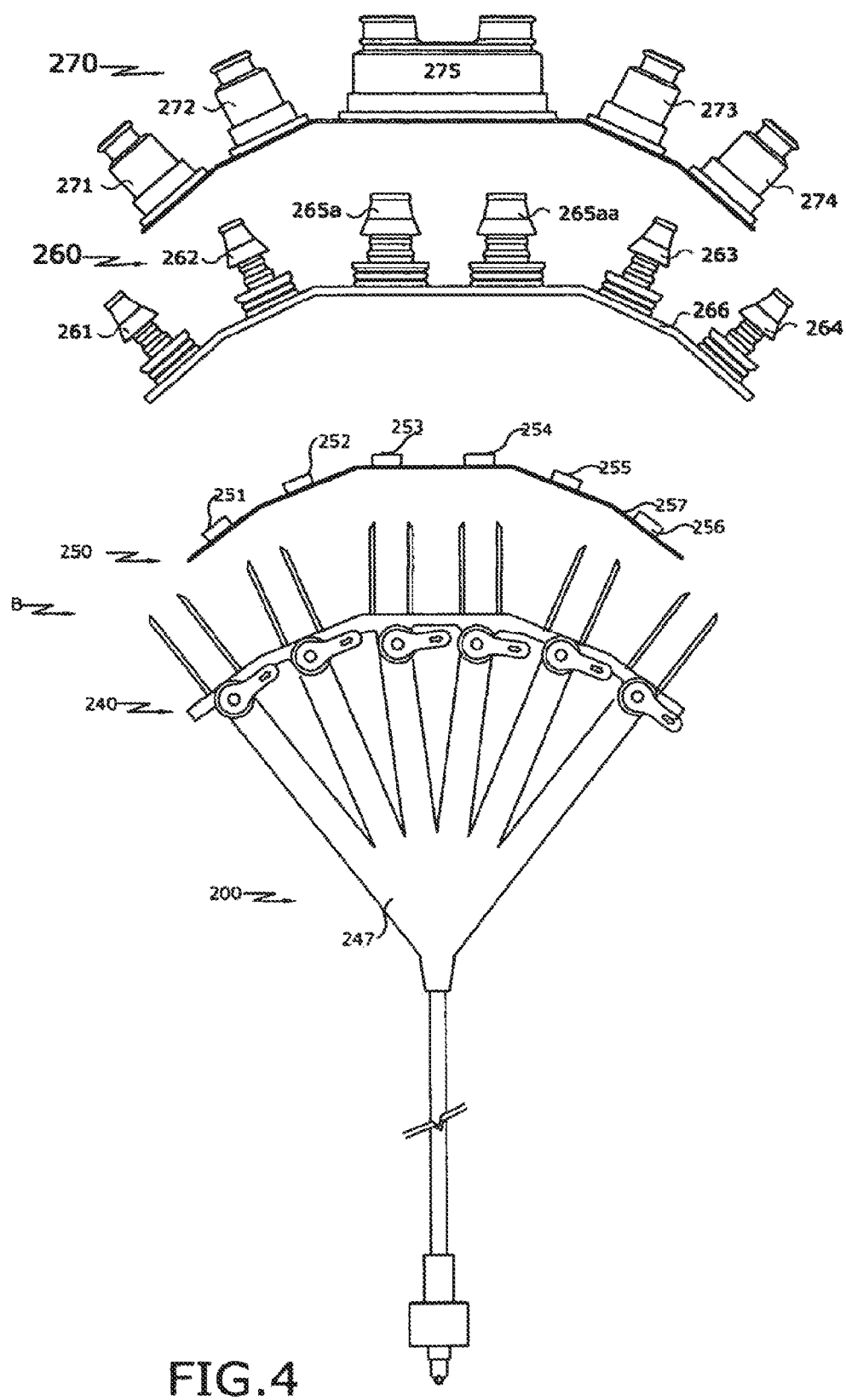
FIG. 4 illustrates in an exploded view the components or parts (layers) from which a multi layer manifold housing, having four layers, may be assembled.

FIG. 4 illustrates a front exploded view of the support housing at the proximal portion (B) of the manifold (200) of FIG. 2. In this embodiment the manifold (200) has six lumens that terminate at the manifold proximal portion (B), four of which are connected to female luer type connectors (271)-(274), and the remaining two lumens are connected to high flow connectors (275). The housing is assembled using a multi layer configuration for establishing a plurality of mutually distinct flow channels (lumens) consisting of the following layers or components: (a) as a first component the distal frame layer (240) of the manifold body (247), at which the isolated lumens terminate, having a plurality of distal frame outlet ports, wherein each distal frame port is positioned above a corresponding proximal inlet port of an isolated lumen, and optionally comprising, as shown in this embodiment, a pair of spikes (248) (249), which protrude from the distal frame; (b) a, lower intermediate gasket layer or component (250) comprising an elongated flat portion (257) and a plurality of lower gasket members (251)-(256), wherein each distal frame port is positioned above a corresponding proximal inlet port of each lumen, respectively. Optionally, apertures are located along the flat portion (257), correspond to the positions of the spikes, in order to allow for passage of the spikes through the apertures when positioning the lower gasket layer (250) on the surface of the proximal frame (247); (c) an upper intermediate gasket layer or component (260) and a plurality of upper gasket members (261), (262), (263), (264), (265a), (265a) protruding from above the flat portion (266), for positioning above proximal inlet port of each lumen, respectively; (d) female luer connector layer or component (270) comprising four female luer type connectors (271), (272), (273), (274) and one double, high flow connector (275). The connectors are hollow, and thus adapted to receive of the upper gasket members from the upper gasket layer (260). After assembling the four layers together, the manifold becomes one integral housing unit, enabling, at its proximal portion four luer type connections and one double tubing high flow connection.

The gasket layers and gasket members may comprise any flexible or resilient material, such as silicone rubber, thermoplastic rubbers, e.g. SEBS, and polyurethanes, for providing fluid communication as well as fluid sealing as described hereinbelow. Nevertheless, any material having equivalent properties are acceptable.

The distal frame layer as well as the female connector layer may be manufactured of any hard or relatively hard resilient plastic, such as polycarbonate polysulfone, ABS, polyurethane, modified acrylic copolymer, e.g. cyrolites. Nevertheless, any material having equivalent properties are acceptable.

Optionally, antiseptic solution and/or an anti-trombolitic agent or any admixture thereof is inserted between at least one set of upper and lower gasket members.

FIG. 5 illustrates an enlarged view of a specific example of a multi layer configuration, wherein the distal frame layer (240) of a manifold (not shown) and the upper gasket layer (260) with upper gasket member (261) are shown. The female luer connector layer is not shown. This embodiment corresponds to the embodiment illustrated in FIG. 6C, i.e. having only the upper gasket layer, thus having three layers in total. The upper gasket member (261) comprises a hollow channel portion (260a) and a shoulder-like outer sleeve portion (260b) protruding from the flat portion (266) of the gasket layer (260). A pair of spikes (248) (249) pass through the outer sleeve portion (260b). These spikes (248), (249) are an integral part of, and protrude from the distal frame layer (240). The free ends of the spikes (248), (249) are situated inside the truncated conical portion (260c) of the gasket member (261). The flat top portion (260d) at the upper end of the truncated conical portion (260c) seals the gasket member (261) when not being accessed by a male connector, and allows fluid to flow through slot or normally closed slit (260e) when a male connector is connected to the gasket member (261). The sides of the slot (260e) sealingly tighten together whenever the gasket member (261) is not accessed by a male connector, thereby allowing the outer surface to be easily swabbed. The interaction between the spikes and the gasket, which open the slot upon connection of a male connector plug is illustrated in FIG. 5A.

FIG. 5A illustrates the interaction between the spikes (248), (249) and the gasket member (261), by which the slot opens upon connection of a male connector, in particular, showing the shape of the gasket member (261), upon exertion of a downwardly directed pressure on the flat top portion (60d). Such pressure is exerted when a male connector is connected to the gasket member (261). When the flat top portion (260d) is pressed downwards, the outer sleeve portion (260b) folds in accordion-like shape, and the conical portion (260c) is stretched outwardly by means of the spikes (248), (249) which penetrate the narrower part of the conical portion (260c), near its top (260d). This maneuver separates the sides of the slot (260e), thus enabling fluid communication between the male and female connectors.

The interaction between the spikes and the gasket is further detailed in FIG. 6C, as described hereinbelow. Similar interactions are also detailed in FIGS. 6A and 6D, and concern other embodiments of the gasket members.

Figure 6A:
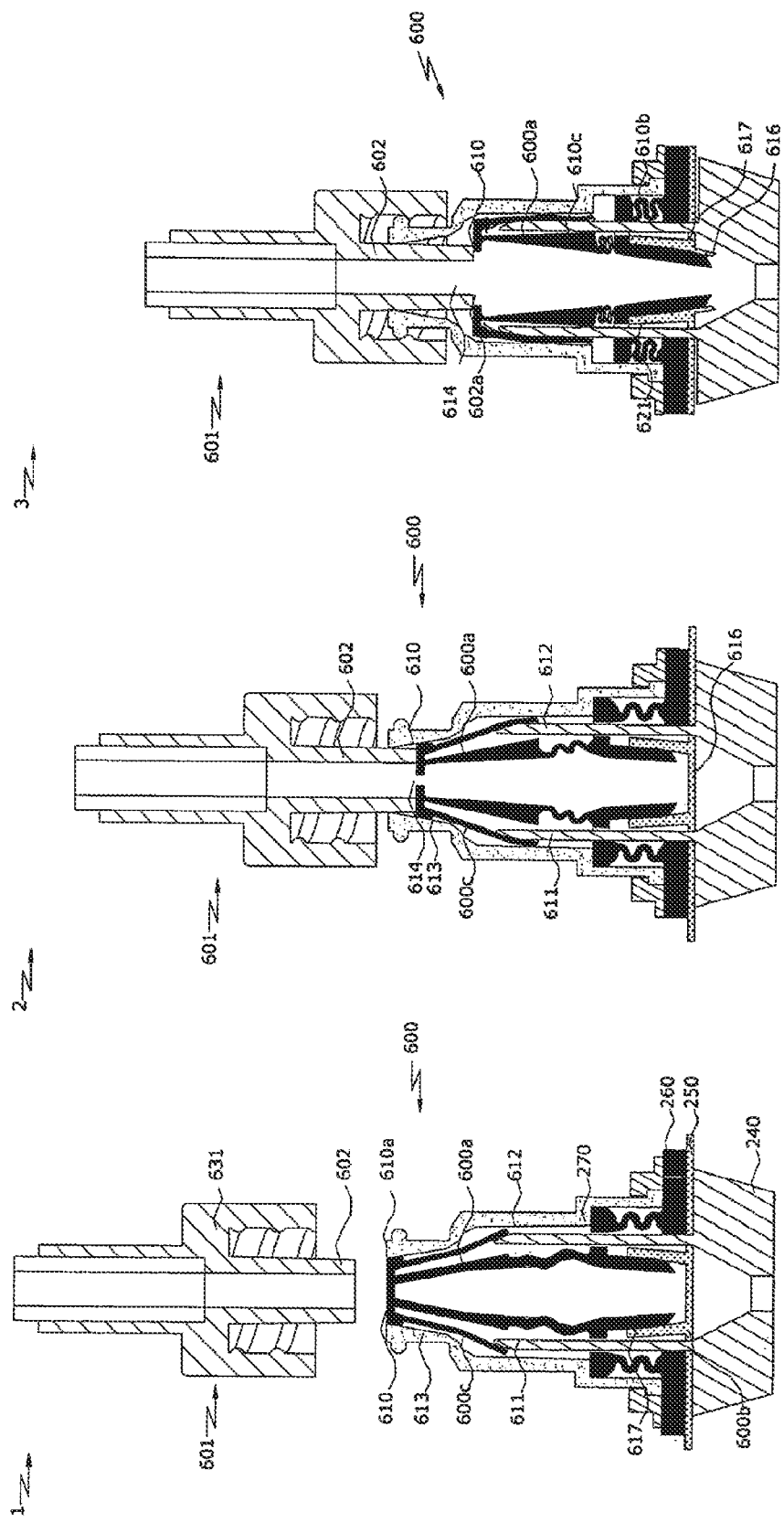

FIG. 6A illustrates three cross sectional views corresponding to three main states, initial (1), middle (2) and final (3) positions, of the upper gasket member (600a) during a interaction between a male and female luer type connectors (601), (600). The support housing is comprised of the same four layers illustrated in the embodiment of FIG. 4, mutatis mutandis: (a) the distal frame layer (240) of the manifold body, (b) a first/lower gasket layer (250); (c) a second/upper gasket layer (260); and (d) a female lure connector layer (270). The male connector (601) is comprised of a rotating flange (631) having a male luer cone (602). In an initial position (1) entry to the proximal inlet port of the lumen (not shown) is blocked by the sealing of both the upper gasket member (600a), the lower gasket member (600b). The conical portion (600c) of the upper gasket member (600a) minimally overlaps the spikes (611) (612), such that in the initial position (1), no stretching forces act to open the slot (not shown in this figure) at the flat top end (610) of the conical portion (600c). Furthermore, in the initial position (1) the flat top portion is situated level with the upper edge (610a) of the neck portion (613). Thus, the flat top portion (610) is pressed inwards, due to the inwardly exerted pressure from the neck walls on the upper end of the upper gasket (600a) and the flat top end (610), thereby sealing the slot.

In a middle position (2), the luer cone (602) of the male connector (601) is partially inserted to the female connector (600), thus exerting pressure over the flat top portion (610)) of the upper gasket member (600a), and thereby forcing the upper gasket member (600a) to slide downwards inside the housing. Simultaneously, the conical portion (600c) further overlaps the spikes (611), (612), which, outwardly stretches the conical portion (600c), and in turn stretches the flat top portion (610). As a result, the slot (614) located in the flat top portion (610) is stretched and slightly opens.

In a final position (3), the male connector (601) is fully threaded over the female connector (600), and its luer cone (602) is fully inserted to the female connector (600). It can be observed how the conical portion of the upper gasket member (600a) fully overlaps the spikes (611), (612), thereby fully stretching the flat top portion (610), which causes the slot (614) to open fully. The outer sleeve portion (610b), as well as the inner portion (610c) of the upper gasket (600a), are both compressed in an accordion like manner as shown in the figures. The outer sleeve portion (610b) and the inner portion (610c), exert an upwardly directed force, which causes the flat top portion (610) to press tightly against the bottom (602a) of the luer cone (602), thereby preventing leakage of fluids between the luer cone (602) and the upper gasket member (600a). Simultaneous with the process described above, the upper part of the cannula like member (621), situated at the lower part of the inner portion (610b) of the upper gasket member (600a), overlaps the upper edge (617) of the lower gasket member (600b), while the lower part (also referred to herein as the "tip") of the cannula like member (621) pushes the sealing surface (616) of the lower gasket downwards to an open position. The cannula-like member (621) additionally comprises an outer and/or inner non-elastic reinforcement useful for an easy and efficient penetration of the tip into the slot.

Figure 6B:
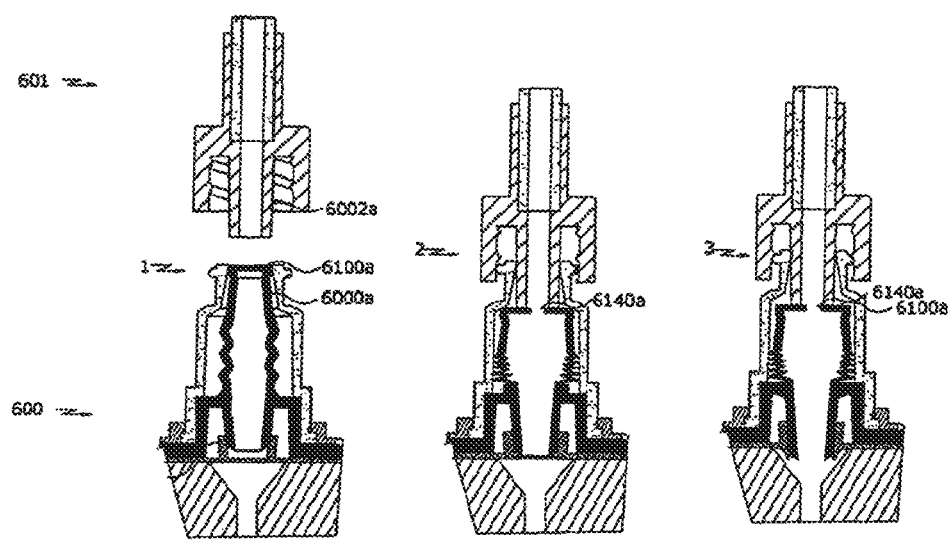

FIG. 6B illustrates another embodiment of three cross sectional views corresponding to three main states, initial (1), middle (2) and final (3) positions of the upper gasket member (6000a) during an interaction between male and female luer type connectors (601), (600), similar to those illustrated in FIG. 6A, mutatis mutandis. This embodiment defers from that of FIG. 6A in that in FIG. 6B, there are no spikes protruding from the distal frame layer (240) of the manifold body, nor is there a conical portion at the upper part of the upper gasket member (6000a). When the male cone (6002a) exerts a downward pressure on the flat top portion (6100a), the upper part of the channel portion of the upper gasket (6000a) is forced outwards, thereby widening the opening of the slot (6140a).

Figure 6C:
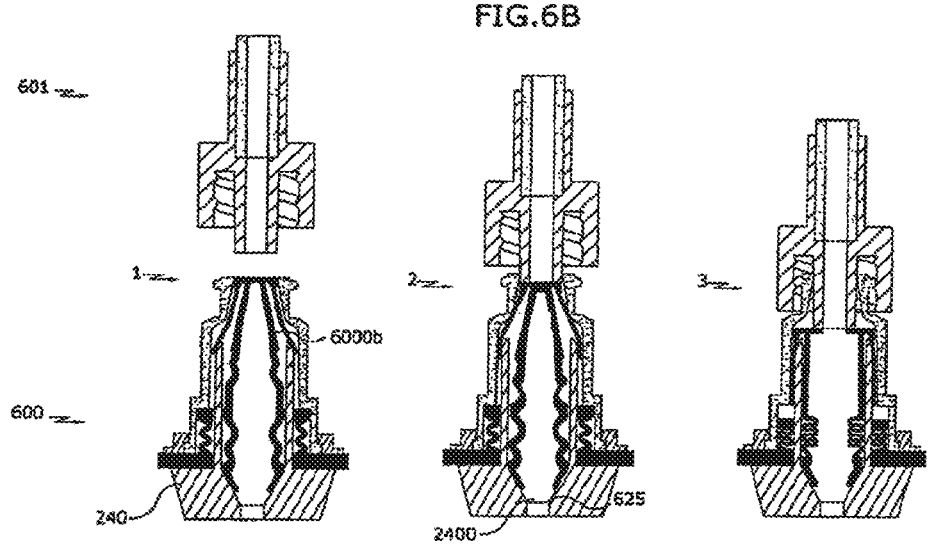

FIG. 6C illustrates another embodiment of three cross sectional views corresponding to three main states, initial (1), middle (2) and final (3) positions of the upper gasket member (6000b) during an interaction between male and female luer type connectors (601), (600), similar to those illustrated in FIG. 6A, mutatis mutandis. This embodiment defers from that of FIG. 6A in that FIG. 6C lacks the first gasket layer. Thus, in the final position (3), the lower part of the channel portion of the gasket (6000b) adheres directly to the inclined lip (625) of the corresponding distal frame layer port (2400) thereby sealing the port (2400) from leakage. Furthermore, the widened channel portion of the gasket (6000b), when compressed in the final position (3) is thickened, thereby further preventing leakage.

Figure 6D:
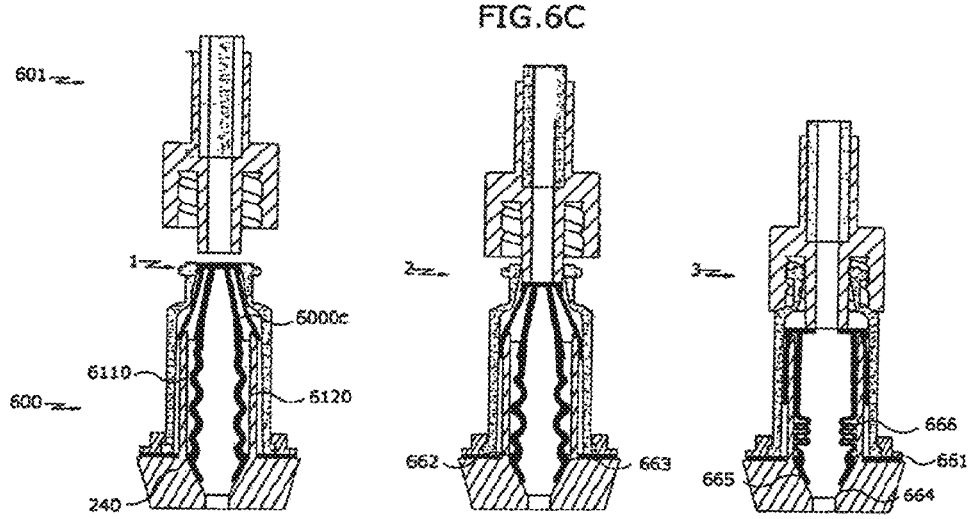

FIG. 6D illustrates three cross sectional views corresponding to three main states, initial (1), middle (2) and final (3) positions of the upper gasket member (6000c) during an interaction between male and female luer type connectors (601), (600), similar to those illustrated in FIG. 6A, mutatis mutandis. This embodiment defers from that of FIG. 6A in that FIG. 6D lacks the first gasket layer, and further defers from the embodiment of FIG. 6A in that the single gasket layer of FIG. 6C lacks the outer sleeve portion through which pass the spikes in FIG. 6A. Accordingly, the spikes (6110), (6120) in this embodiment pass through apertures (662), (663) in the flat layer (661) of this gasket member (6000c). In the final position (3), the lower part (665) of the channel portion of the gasket member (6000c) is positioned along the inclined lip (664) of the distal frame layer (240).

FIG. 6E illustrates two cross sectional views corresponding to two main states, initial (1) and final (3) positions of the upper gasket member (6000d) during an interaction between male and female luer type connectors (601), (600), similar to those illustrated in FIG. 6A in initial position (1) and final position (3), mutatis mutandis. This embodiment differs from that of FIG. 6A in that FIG. 6E does not have spikes protruding from the distal frame layer (240) of the manifold body. FIG. 6E further differs in that the channel portion of the upper gasket member (6000d) does not have folds for compressing in an accordion-like manner, and, as such, only the outer sleeve portion (6100b) of the upper gasket member (6000d) is compressed. FIG. 6E further differs from FIG. 6A in that the lower edge of the cannula-like member (621) is square for fitting into the step (672) that exists at the port of the distal frame layer (240), as shown in the final position (3).

FIG. 6F illustrates two cross sectional views corresponding to two main states, initial (1) and final (3) positions of the upper gasket member (6000d) during an interaction between male and female luer type connectors (601), (600), similar to those illustrated in FIG. 6E in initial position (1) and final position (3), mutatis mutandis. This embodiment defers from that of FIG. 6E in that the housing in FIG. 6F does not have a first gasket layer.

In all of the above embodiments, when a male connector is removed from a port, the gaskets retract to their initial position and re-seals the female ports until another connection of a male connector is made.

Figure 7A:
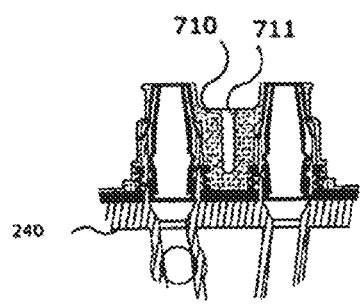
FIGS. 7A, 7D, 7E, and 7F, illustrates four different embodiments of multi layer construction of double tubing connectors corresponding to the four embodiments of FIGS. 6A, 6B, 6C and 6D.
Figure 7B:
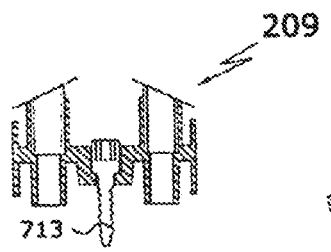
FIG. 7B illustrates one embodiment of a double tubing male connector according to the present invention.
Figure 7C:
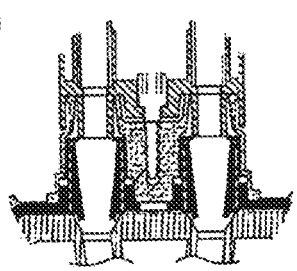
FIG. 7C illustrate the double tubing connector of FIG. 7A, accessed by the male connector of FIG. 7B.
Figure 7D:
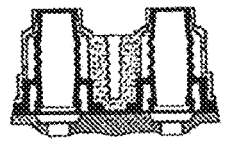

FIG. 7A illustrates a cross sectional view of a double port of the manifold of the present invention, adapted for receiving a corresponding double tubing high flow plug. The layers of the housing of the double port may be similar to those illustrated in FIGS. 6A to 6F, mutatis mutandis except the double port has a larger diameter bore, useful for allowing greater fluid flow rates. The double port differs, however, from the embodiments of FIGS. 6A to 6F in that the distal frame layer of the manifold is adapted for the connection of a double tubing plug, and for securing the plug to the manifold by means of a clamp and/or a screw. An elevated bridge (710) is provided between each connector of the double connector, having an aperture (711) for receiving a screw. FIG. 7B illustrates the double male connector (209) with a screw (713), and FIG. 7C illustrates the double male connector (209) connected to the female connector and secured by the screw that is fastened in the aperture (711). Alternatively, although not shown in the figures, any similar method of connecting the male to the female connector may be utilized.

FIGS. 7A, 7D, 7E and 7F, correspond to the structures of the proximal and lower gasket members of FIGS. 6A, 6B, 6C and 6D, respectively, showing the gasket members in an initial position.

Figure 7G:
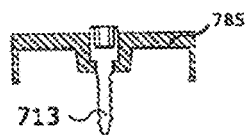
FIG. 7G illustrates one embodiment of a cover for double tubing female connector according to the present invention.
Figure 7H:
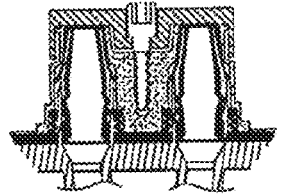
FIG. 7H illustrate the double tubing connector of FIG. 7A, covered by the cover illustrated in FIG. 7G.
Figure 7E:
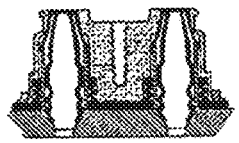

FIGS. 7G and 7H illustrate a cover (785) for the double female connector that can be secured to the double connector when not in use, in order to protect the double connector from hazards and contamination.

Figure 7I:
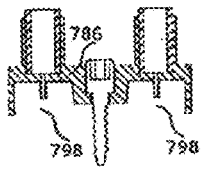
FIG. 7I illustrates one embodiment of a double tubing infusion male connector according to the present invention.
Figure 7J:
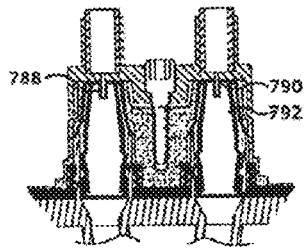
FIG. 7J illustrate the double tubing connector of FIG. 7A, accessed by the infusion male connector of FIG. 7I.
Figure 7F:
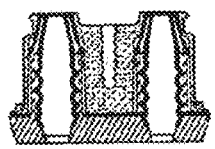

FIGS. 7I and 7J illustrate a cover (786) similar to that shown in FIGS. 7G and 7H, having pins (798) for piercing through the slots (788) located at the flat top portion (790) of the upper gasket member (792), sealing the connectors when not in use. When necessary, access to the female double connectors without pushing the upper gasket member (792) downwards in order to fully open the slots, is possible through the pins (798). This type of access is necessary for some kinds of patient treatments (e.g. for dripping purposes).

FIG. 8A illustrates a manifold extension member (800). The extension member is comprised of a multi lumen connector (801) corresponding to the multi lumen port of a manifold (810), and a multi lumen tube (802) which ends with a multi lumen tip (803) and a connector flange (804) together being an outlet connector (805), for connecting to any device or equipment having a corresponding connector.

FIG. 8B illustrates two cross sectional views (802a) and (802b) of the multi lumen tube (802) of FIG. 8A, taken in along E-E and F-F respectively.

FIG. 8C illustrates an enlarged view of outlet connector (805) of FIG. 8A.

FIG. 8D illustrates a front view of the tip (803) of the multi lumen tube of FIG. 8A.

FIG. 8E illustrates another embodiment of an outlet connector (815) which differs from the outlet connector (805) of FIG. 8A, in that the outlet of FIG. 8E is the outlet for a plurality of isolated single lumen tubes (812a)-(812e), and in that the outlet of FIG. 8E ends in a single lumen cone (813) similar to that of (170b), in the converging adapter of FIG. 1G.

FIG. 8F illustrates the back terminals (812f)-(812j) of the outlet connector (815), which allows for a separate connection of the end each of the tubes (812a)-(812e) to the outlet connector. The outlet connector (815), the plurality of tubes (812a)-(812e), and an appropriate multi lumen plug at the opposite end of the tubes matching the multi lumen port of a corresponding manifold (see for example FIG. 1F), is another embodiment of a manifold extension member.

Figure 9:
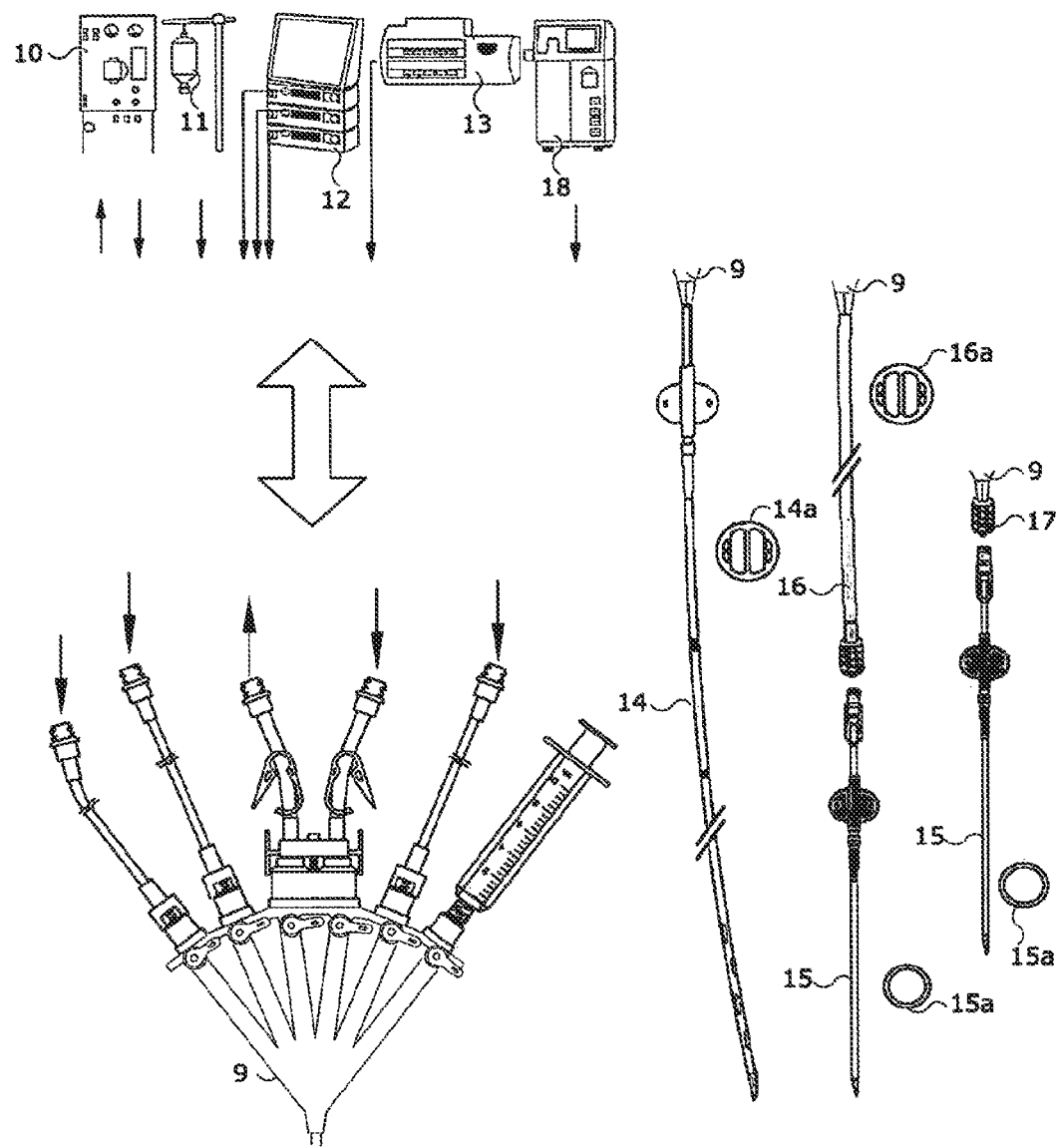
FIG. 9 illustrates several embodiments of systems using a manifold according to the present invention.

FIG. 9 illustrates examples of patient administration systems utilizing the manifold of the present invention, in three different configurations. The manifold may be connected to peripheral elements and devices such as Hemodialysis-Hemofiltration machine (10); Gravitational IV (11); Multi IV-Pump (12) Syringe-Pump (13) and Volumetric and Peristaltic Pump (18). A patient invasive member, such as Manifold/Hub Catheter version (14), could be either integral to the manifold (9) or connected to its multi lumen port via an appropriate connector. Alternatively, a single lumen Catheter (15) may be connected to the multi lumen port through a manifold extension member (16), or through a converging adapter (17). For purpose of clarity cross sectional views (14a), (15a), (16a) of (14), (15) and (16) respectively, are shown.

FIGS. 10 to 15 illustrate additional embodiments of the present invention, comprising essentially all of the features of all of the previous embodiments, mutatis mutandis, with the differences described in detail herein below. As mentioned above, one requirement of fluid administration systems includes priming the manifold lumens by inserting a desired fluid to the manifold. The embodiments shown in FIGS. 10 to 15 describe preferred embodiments of the present invention, wherein the proximal housing unit further comprises features that allow priming the manifold lumens.

FIG. 10 shows the front assembled view of one embodiment of the priming manifold (1000) of the present invention. The manifold (1000) comprises four isolated lumens (1016), (1026), (1036) and (1046) and a housing (1001) having five female luer connectors (1010), (1020), (1030), (1040), (1050), of which four connectors (1010), (1020), (1030), (1040) are respectively situated at the proximal inlet port of each isolated lumen. The housing (1001) further comprises five valves (or, stopcocks) (1015), (1025), (1035), (1045), (1055), corresponding to each connector. The valves (1015), (1025), (1035), (1045), (1055), are shown in four different positions, wherein a first valve (1015) is in the priming position, a second valve (1025) is in the fluid flow position, a third valve (1035) is in the closed position and a fourth valve (1045) is in the flushing position. The priming connector (1050), shown in the fluid flow position, is not in communication with a lumen of the manifold (1000).

The manifold housing (1001) of FIG. 10 is shown in FIG. 10A in an exploded view, and comprises essentially all of the features shown in FIG. 4, mutatis mutandis, with the following differences. In FIG. 10A the distal frame layer (1400) comprises five valves, each of which is situated below an distal frame port (1410), (1420), (1430), (1440), (1450) of the distal frame layer (1400), as seen in FIG. 10B, which shows a top plan view of the distal frame layer (1400). Priming ports (1451), (1452), (1453), (1454), (1455) are shown in fluid communication with one another via priming groove (1450'), as will be described herein below. According to some embodiments, the lower gasket layer (1300) of FIG. 10B comprises gasket extensions (1311) (shown in FIG. 12A) that depend downward from the lower gasket layer (1300), for inserting into each priming port, thereby enabling one-directional flow of the priming fluid, as will be described herein below. The upper gasket layer (1200) comprises an aperture (1371) (shown in FIG. 12A) along the flat portion of the layer (1200), for inserting a rigid stem (1111) that depends downward from the female luer connector, thereto, as will be described herein below.

Figure 11C:
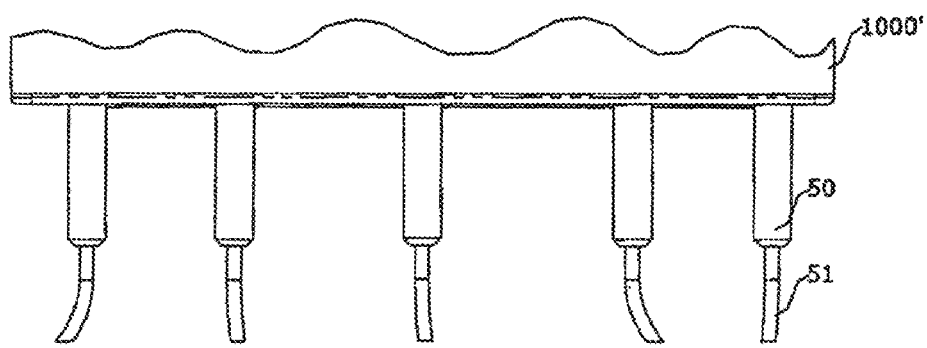
Figure 11D:
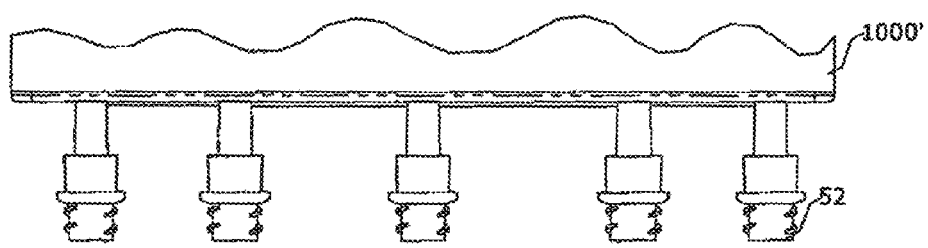
Figure 11E:
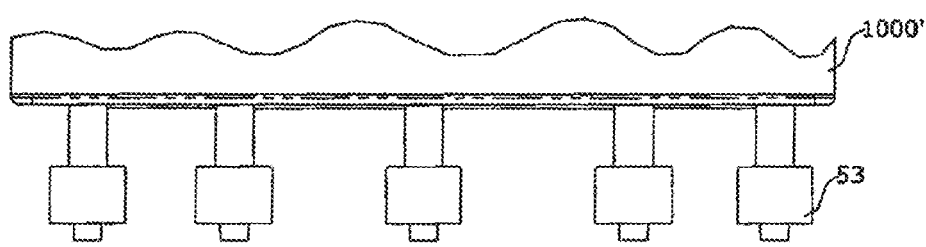

FIGS. 11, 11A and 11B illustrate the front view of another embodiment of the manifold, and comprise essentially all of the features shown in FIGS. 10, 10A and 10B, with the following differences. In the embodiment shown in FIGS. 11, 11A and 11B the manifold housing (1002) essentially comprises a linear shape. FIGS. 11C, 11D and 11E show alternative arrangements of the linear housing, but may be adapted to any housing configuration. FIG. 11C shows the distal frame layer (1000') comprising integral outlet ports (50) with permanently connected lumens (51). FIG. 11D shows the outlet ports (52) comprising female luer connectors. FIG. 11E shows the outlet ports (53) of FIG. 11D, comprising male luer connectors.

Figure 12A:
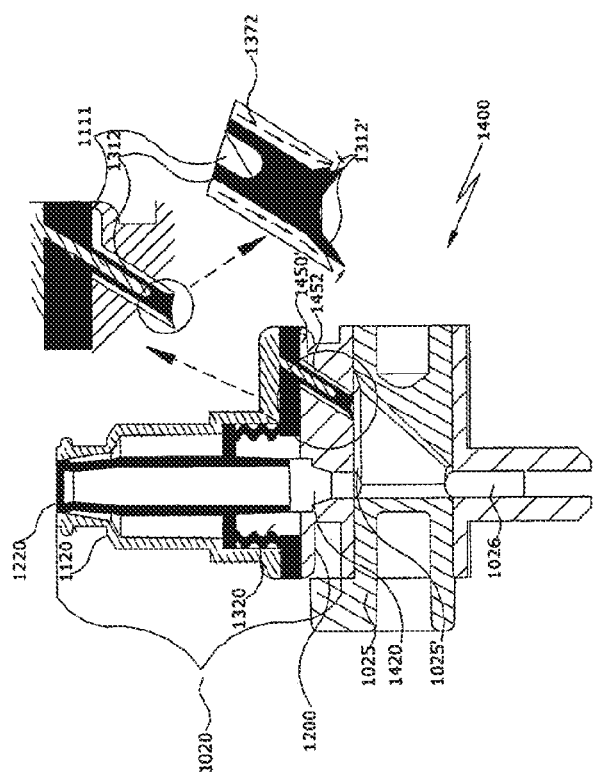
FIG. 12A shows a longitudinal cross sectional view of the proximal end of one lumen of the priming manifold of the present invention, with the stopcock valve for the female connector in the priming position.
Figure 12B:
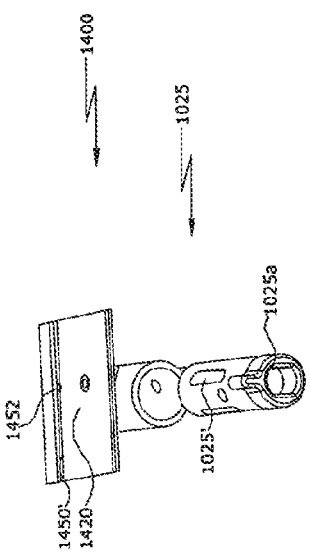
FIG. 12B illustrates a stopcock valve of the priming manifold of the present invention in an exploded perspective view, in the priming position.

FIG. 12A shows a longitudinal cross sectional side view of an assembled luer connector (1010), cut along the central axis of the connector (1010) in a plane orthogonal to the plane shown in the figure. FIG. 12B shows the valve (1015) with the positioning member (1015a) unassembled. The valve (1015) shown in FIGS. 12A and 12B is in the priming position, whereby the priming port (1451) is in fluid communication with the lumen (1016) due to the alignment of the transfer conduit (1015') of the valve (1015) within the distal frame layer (1400). One-directional flow of the priming fluid is achieved via a check valve arrangement, wherein the gasket extension (1311) that depends downward from the lower gasket layer (1300), and the rigid stem (1111) that depends downward from the female connector layer (1100), and is inserted to the gasket extension (1311) for support. The extension (1311) and stem (1111) are lodged in the priming port (1451). Flange (1311') extends outward. When priming fluid flows (shown by arrows (1372)) through the priming port (1451) from the priming groove (1450'), the flange (1311') bends in the direction of the flow. The fluid continues to flow through the transfer conduit (1015') and into the lumen (1016), thereby priming the lumen. Fluid flowing through the transfer conduit (1015') in the retrograde direction would cause the flange (1311') to close the priming port (1451), and not allow any fluid to enter therein.

FIG. 12A' and 12B' show a cross section of the luer connector (1020) and the valve (1025) in a similar view as that of FIGS. 12A and 12B, mutatis mutandis, with the following differences. One-directional flow of the priming fluid is achieved via the gasket extension (1312) that depends downward from the upper gasket layer (1200), and the rigid stem (1112) that depends downward from the female connector layer (1100), and is inserted to the gasket extension (1312) for support. The extension (1312) and stem (1112) are lodged in the priming port (1452). Flange (1312') extends outward. When priming fluid flows (shown by arrows (1372)) through the priming port (1452) from the priming groove (1450'), the flange (1311') bends in the direction of the flow. The fluid continues to flow through the transfer conduit (1025') and into the lumen (1026), thereby priming the lumen. Fluid flowing through the transfer conduit (1025') in the retrograde direction would cause the flange (1312') to close the priming port (1452), and not allow any fluid to enter therein.

FIGS. 13A and 13A' show a cross section of the luer connector (1020) and the valve (1025) in a similar view as that of FIGS. 12A and 12B, mutatis mutandis, with the following differences. The valve (1025) is in the fluid flow position, which allows fluid communication between the distal frame port (1420) of the distal frame layer (1400) and the lumen (1026). The priming port (1452) is sealed, thereby not allowing priming to take place.

FIGS. 13B and 13B' show a cross section of the luer connector (1030) and the valve (1035) in a similar view as that of FIGS. 12A and 12B, mutatis mutandis, with the following differences. The valve (1035) is in the closed position, such that no fluid communication within the housing is possible.

FIGS. 13C and 13C' show a cross section of the luer connector (1040) and the valve (1045) in a similar view as that of FIGS. 12A and 12B, mutatis mutandis, with the following differences. The valve (1045) is in the flushing position, wherein the priming port (1454) is in fluid communication with the distal frame port (1440) of the distal frame layer (1100) via transfer conduit (1045'). Priming fluid is introduced to the housing after use, and remains in place until reuse, when the fluid is removed from the manifold by flowing through the lumen.

FIGS. 13D and 13D', and FIGS. 13E and 13E' show a cross section of the priming connector (1050) and the valve (1055) in a similar view as that of FIGS. 12A and 12B, mutatis mutandis, with the following differences. The priming valve (1055) is shown in its open and closed positions respectively. In the open position (FIGS. 13D and 13D'), the priming fluid is fed into the priming connector (1050) and enters the distal frame port (1450) of the distal frame layer (1100). The priming fluid continues to flow within the transfer conduit (1055'), up the priming port (1455) and into the priming groove (1450'). The fluid flows through the priming groove (1450') to the priming ports located along the distal frame layer (1100) in order to prime their respective lumens. In the valve's (1055) closed position (FIGS. 13E and 13E'), fluid communication between the upper port of the distal frame layer (1100) and the priming port (1455) is not possible.

FIGS. 14A, 14B, 14C, 14D and 14E illustrate another embodiment of a manifold housing, comprising essentially all of the features shown in the previous embodiments of the priming manifold, in particular, the same four housing layers or components, mutatis mutandis, with the following differences. In FIGS. 14A, 14B, 14C and 14D the housing comprises four female luer connectors (2110)-(2140), a double high flow port (2051) having two female non-luer connectors (2050a), (2050b) and a priming connector (2050c).

In the exploded view of the housing shown in FIG. 14B, in the distal (lower) frame layer or component shown in FIG. 14B, and the top plan view shown in FIG. 14C, an additional middle priming port (2455c) is situated along the priming groove (2450'), for directly filling the priming groove with priming fluid, as will be described herein below. The lower intermediate gasket layer or component (2300) comprises two large gasket members (2350a), (2350b) for accommodating the high flow connectors, and an additional gasket (2350c) is situated along the lower intermediate gasket layer, above the middle priming port (2455c). The female luer connector layer or component (2100), shown in top plan view in FIG. 14D, comprises aperture (2711) for receiving a screw, similar to that shown in FIG. 7A, mutatis mutandis, in order to hold a fitting of the types shown in FIG. 7. As shown in FIG. 14A-E, the manifold hub is comprised of a housing composed of four components, namely, a rigid connector component, an upper resilient intermediate gasket component, a lower resilient intermediate gasket component and a distal frame layer or component. A plurality of mutually distinct flow channels are established through the housing and valves are associated with the plurality of distinct flow channels. The mechanism of how the gaskets, via the normally closed slits, maintain the flow channels open or closed has been previously described in detail.

FIG. 14E shows a cross section of the luer connector (2050c) in a similar view as that of FIG. 12A, mutatis mutandis, with the following differences. The port (2455c) is situated along the priming groove (2450'). Thus, priming fluid that is inserted to the connector (2050c) flows directly to the priming groove (2450'). Additionally, in FIG. 14E, a valve is not present for opening and closing the port.

Figure 15:
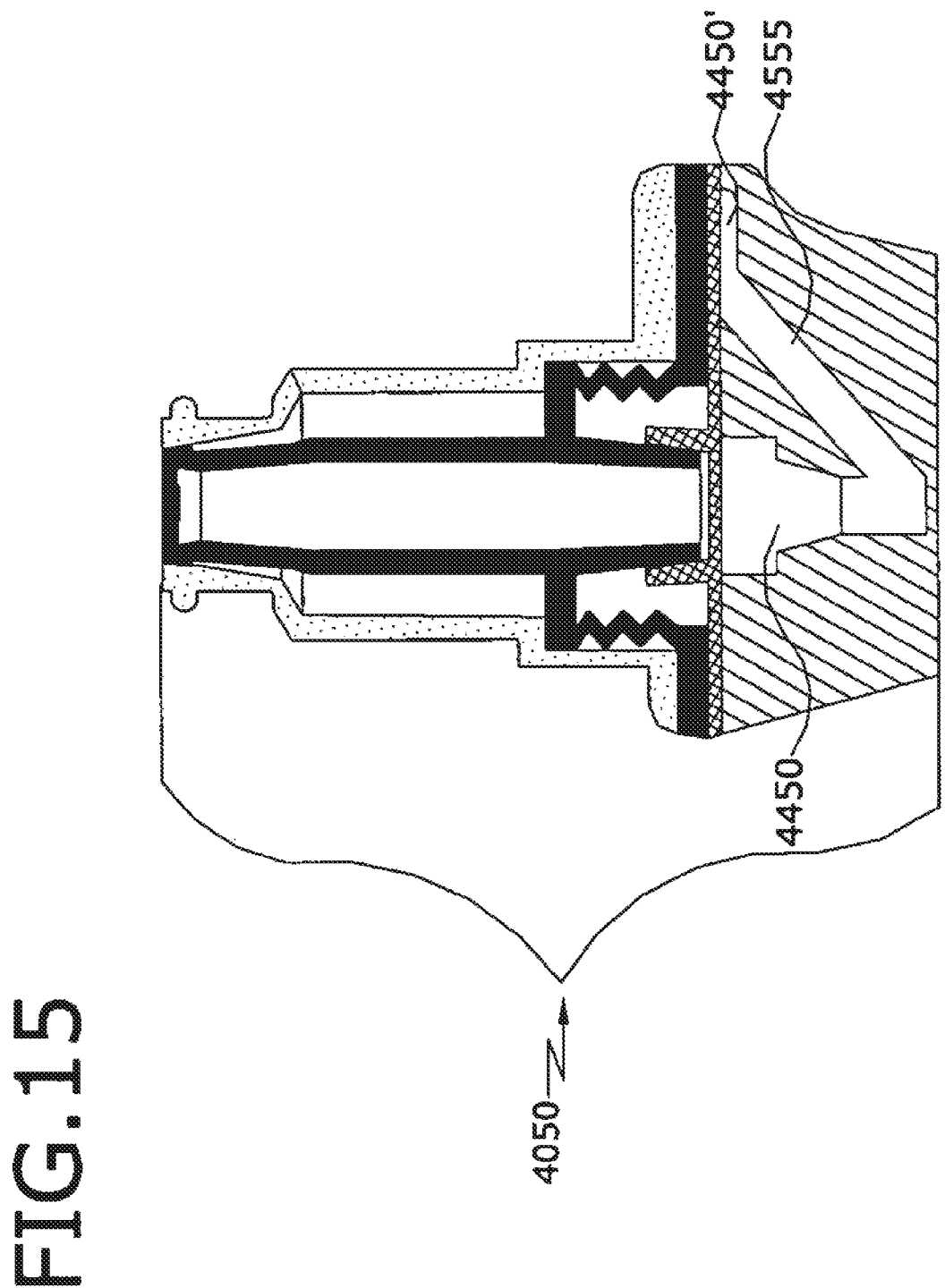
FIG. 15 illustrates an embodiment of the priming connector of the present invention, wherein the pressure of the priming fluid as it is inserted to the priming connector causes the fluid to flow along the priming groove, and thereby enter the priming ports.

FIG. 15 shows another embodiment of the priming connector (4050) wherein the distal frame layer does not comprise a valve. Thus, priming fluid is inserted to the connector (4050) and flows from the distal frame port (4450) of the distal frame layer to the priming port (4450') via the priming groove (4555).

Figure 16:
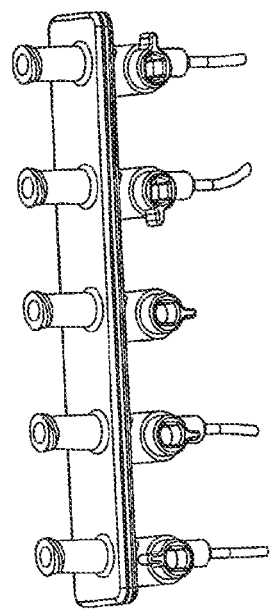
FIGS. 16, 16A and 16B illustrate a further embodiment of the priming manifold of the present invention, wherein the female connector is non-luer activated, and the gasket layer does not comprises gasket members.
Figure 16A:
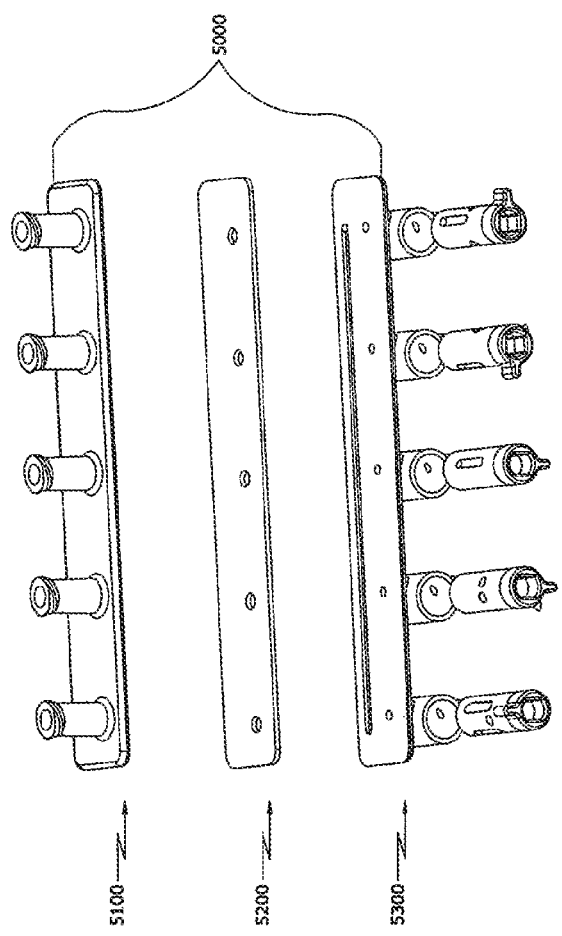
Figure 16B:
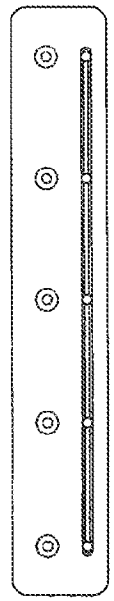

FIGS. 16, 16A and 16B show an alternative embodiment of the priming housing of the present invention, similar to that shown in FIGS. 11, 11A and 11B, mutatis mutandis, wherein the housing is shown with only one gasket layer (5200), and comprising a female connector layer (5100) whose female connectors are not the luer activated type, and is just meant to be utilized as a priming housing for the manifold.

FIGS. 17A, 17B, 17C and 17D illustrate another embodiment of a manifold housing, comprising essentially all of the features shown in the embodiments of FIGS. 14A, 14B, 14C, 14D and 14E, in particular, the same four housing layers, mutatis mutandis, with the following differences. In FIGS. 17A, 17B, 17C and 17D the distal frame layer does not comprise valves. FIG. 17B, shows a cross section of the luer connector (3371) in a similar view as that of FIG. 12A, mutatis mutandis, however, in FIG. 17B, no valve is shown.

According to all embodiments, the distal frame layer optionally does not comprise any valves for regulating the fluid flow through the connectors. Alternatively, some valves may be present for regulating fluid flow through some connectors. Additionally, it is appreciated that the priming connector is not required to be located at any particular location along the housing, and that the positions described herein are for illustrative purposes only.

The invention claimed is:

1. A manifold hub for use in a fluid administration system comprising:
   A. an integrated housing providing a plurality of mutually distinct flow channels through the housing and being composed of at least three components;
      i. a first component comprised of a first member having a plurality of spaced first openings each associated with a distinct flow channel and a plurality of spaced upward, tubular first projections surrounding and aligned with said first openings and open at their upper and lower extremities each associated with a distinct flow channel, said first projections formed as one part of a two-part connector;
      ii. a second component comprised of a second member having a plurality of spaced second openings each associated with a distinct flow channel and defining a plurality of spaced separate outlets each associated with a distinct flow channel;
      iii. an intermediate component comprised of a third member being resilient and having a plurality of spaced third openings each associated with a distinct flow channel and a plurality of spaced upward annular second projections each associated with a distinct flow channel, each second projection surrounding a respective third opening, said second projections having closures at their upper extremities with normally closed slits defined in said closures and being open at their lower extremities;
   B. said first, second and third components being arranged together with the intermediate component between the first and second components and integrated together to form said housing (a) with said second projections received in the first projections with the closures at the upper extremities of the second projections exposed at the upper extremities of the first projections, (b) the second openings and the third openings being in fluid communication, (c) the integrated components establishing the plurality of mutually distinct flow channels through the housing, and (d) the mutually distinct flow channels sealed one from the other;
   C. whereby each said first projection can be connected to a fluid administration set via a terminal complementary part to said one part of the two-part connector such that when the connector is complete, the normally closed slit defined in the closure at the upper extremity of the resilient second projection is opened; and
   D. whereby the separate outlets of the second component can be connected to separate lumens each terminated with its own element for infusing fluid into a patient.

2. The invention of claim 1 further including a plurality of valves mounted in the housing upstream of the plurality of spaced separate outlets for controlling fluid flow through the plurality of mutually distinct flow channels, with each said valve associated with a distinct flow channel.

3. The invention of claim 1 wherein the second component includes a reservoir and the housing includes a fluid channel for introducing fluid to said reservoir, and a plurality of passageways placing said reservoir in fluid communication with said plurality of separate outlets.

4. The invention of claim 3 wherein check valves are interposed in the plurality of passageways.

5. The invention of claim 3 wherein control valves are mounted in the housing upstream of the separate outlets and in communication with the plurality of passageways for controlling fluid flow in each channel by priming said channel, flushing said channel, shutting off said channel, and enabling flow through said channel.

6. The invention of claim 1 wherein at least one of the mutually distinct flow channels has a higher flow capacity than other flow channels and wherein the first projection associated with the at least one flow channel is provided with a fitting mounted on said first component for controlling flow through said at least one flow channel.

7. The invention of claim 1 wherein a second intermediate component is provided between the first intermediate component and the second component, said second intermediate component is resilient and has a plurality of spaced fourth openings aligned with the second openings of the second component and constitute part of the mutually distinct flow channels.

8. The invention of claim 7 wherein said fourth openings of said second intermediate component are in the form of normally closed slits surrounded by open upstanding tubular third projections into which are received the lower open extremities of said annular second projections, and wherein the lower extremity of the second projection coacts to open the normally closed slit of the fourth opening in said flow channel.

9. The invention of claim 7 further including a plurality of valves mounted in the housing upstream of the plurality of spaced separate outlets for controlling fluid flow through the plurality of mutually distinct flow channels, with each said valve associated with a distinct flow channel.

10. The invention of claim 7 wherein the second component includes a reservoir and the housing includes a fluid channel for introducing fluid to said reservoir, and a plurality of passageways placing said reservoir in fluid communication with said plurality of separate outlets.

11. The invention of claim 10 wherein check valves are interposed in the plurality of passageways.

12. The invention of claim 10 wherein control valves are mounted in the housing upstream of the separate outlets and in communication with the plurality of passageways for controlling fluid flow in each channel by priming said channel, flushing said channel, shutting off said channel, and enabling flow through said channel.

13. A hub for use in a fluid administration system comprising:
  A. a housing providing at least two mutually distinct flow channels through the housing and being composed of at least three components;
    i. a first component comprised of a first member having at least two separate first openings each associated with a distinct flow channel and at least two of tubular first projections surrounding and aligned with said first openings and open at their upper and lower extremities each associated with a distinct flow channel, said first projections formed as one part of a two-part connector;
    ii. a second component comprised of a second member having at least two second openings each associated with a distinct flow channel and defining at least two separate outlets each associated with a distinct flow channel;
    iii. a third valve component interposed between the first and second components associated with the distinct flow channels for controlling flow through the distinct flow channels;
  B. said first, second and third components forming said housing (a) with the components establishing the at least two mutually distinct flow channels through the housing, and (b) the mutually distinct flow channels being sealed one from the other;
  C. whereby each said first projection can be connected to a terminal complementary part of a two-part connector such that when the connector is complete fluid can flow through the at least two distinct flow channels under the control of the valve component; and
  D. whereby the separate outlets of the second component can be connected to separate lumens each terminated with its own connection element for fluid flow relative to a patient.

14. The invention of claim 13 wherein the housing includes a reservoir and a fluid channel for introducing fluid to said reservoir, and a plurality of passageways placing said reservoir in fluid communication with said plurality of separate outlets.

15. The invention of claim 14 wherein check valves are interposed in the plurality of passageways.

16. The invention of claim 13 wherein the third valve component is in communication with the plurality of passageways for controlling fluid flow in each distinct flow channel by priming said channel, flushing said channel, shutting off said channel, and enabling flow through said channel.

17. The invention of claim 13 wherein two fittings are mountable on adjacent first projections, one for enabling flow through the distinct flow channels associated with both adjacent first projections, and one for shutting off flow through the distinct flow channels associated with both adjacent first projections and protecting against contamination.

18. A method for manufacturing a housing for supporting proximal inlet ports of a plurality of isolated flow channels, for use in a patient fluid administration system, wherein each of said flow channel further comprises a distal outlet for connecting to a patient fluid administration member comprising the steps of:
  a. providing a first component comprised of a first member having a plurality of spaced first openings each associated with a distinct flow channel and a plurality of spaced upward, tubular first projections surrounding and aligned with said first openings and open at their upper and lower extremities each associated with a distinct flow channel, said first projections formed as one part of a two-part connector;
  b. providing a second component comprised of a second member having a plurality of spaced second openings each associated with a distinct flow channel and defining a plurality of longitudinally spaced separate outlets each associated with a distinct flow channel;
  c. providing an intermediate component comprised of a third member being resilient and having a plurality of spaced third openings each associated with a distinct flow channel and a plurality of spaced upward annular second projections each associated with a distinct flow channel, each second projection surrounding a respective third opening, said projections having closures at their upper extremities with normally closed slits defined in said closures and being open at their lower extremities;
  d. arranging said first, second and third components together with the intermediate component between the first and second components and integrated together to form said housing;
  e. positioning said second projections in the first projections with the closures at the upper extremities of the second projections exposed at the upper extremities of the first projections;
  f. placing the second openings and the third openings in fluid communication;
  g. establishing the integrated components as a plurality of mutually distinct flow channels through the housing;
  h. sealing the mutually distinct flow channels one from the other by the intermediate component;
  i. whereby each said first projection can be connected to a fluid administration set via a terminal complementary part to said one part of the two-part connector such that when the connector is complete, the resilient second projection received in said first projection is depressed downwardly forcing the normally closed slit defined in the closure at the upper extremity thereof to open; and
  j. whereby the separate outlets of the second component can be connected to separate lumens each terminated with its own element for infusing fluid into a patient.

19. The method of claim 18 including the further step of mounting a plurality of valves in the housing upstream of the plurality of spaced separate outlets for controlling fluid flow through the plurality of mutually distinct flow channels, and associating each said valve with a distinct flow channel.

20. The method of claim 19 including the further steps of defining in the second component a groove extending laterally offset from the plurality of spaced second openings, and defining in said second component passageways extending from said groove to said valves for controlling fluid flow in each distinct flow channel by priming said channel, flushing said channel, shutting off said channel, and enabling flow through said channel.

* * * * *